United States Patent
Ratner

(10) Patent No.: US 12,064,551 B2
(45) Date of Patent: *Aug. 20, 2024

(54) OPTIMIZED BREATHING ASSISTANCE DEVICE

(71) Applicant: MERCURY ENTERPRISES, INC., Clearwater, FL (US)

(72) Inventor: Jeffrey B. Ratner, Pinellas Park, FL (US)

(73) Assignee: MERCURY ENTERPRISES, INC., Clearwater, FL (US)

( * ) Notice: Subject to any disclaimer, the term of this patent is extended or adjusted under 35 U.S.C. 154(b) by 51 days.

This patent is subject to a terminal disclaimer.

(21) Appl. No.: 17/834,934

(22) Filed: Jun. 8, 2022

(65) Prior Publication Data

US 2022/0296832 A1    Sep. 22, 2022

Related U.S. Application Data

(63) Continuation of application No. 15/161,610, filed on May 23, 2016, now Pat. No. 11,383,054, which is a
(Continued)

(51) Int. Cl.
| A61M 16/00 | (2006.01) |
| A61M 16/04 | (2006.01) |
| A61M 16/06 | (2006.01) |
| A61M 16/08 | (2006.01) |
| A61M 16/12 | (2006.01) |
| A61M 16/20 | (2006.01) |

(52) U.S. Cl.
CPC .... *A61M 16/0096* (2013.01); *A61M 16/0057* (2013.01); *A61M 16/04* (2013.01);
(Continued)

(58) Field of Classification Search
CPC .......... A61M 16/0057; A61M 16/0096; A61M 16/04; A61M 16/06; A61M 16/0816;
(Continued)

(56) References Cited

U.S. PATENT DOCUMENTS

| 4,495,946 A | 1/1985 | Lemer |
| 4,537,188 A | 8/1985 | Phuc |

(Continued)

FOREIGN PATENT DOCUMENTS

EP    1743671 A1 *  1/2007  ........ A61M 15/0021

OTHER PUBLICATIONS

Chantrel, "17834934_2023-11-16_EP_1743671_A1_M.pdf", Jan. 17, 2007 (Year: 2007).*

*Primary Examiner* — Tu A Vo
*Assistant Examiner* — Alexander Morales
(74) *Attorney, Agent, or Firm* — Larson & Larson; Frank Liebenow; Justin P. Miller

(57) ABSTRACT

A breathing assistance device with improved pressure characteristics provides a high level of CPAP per unit of supplementary respirable gas consumed while maintaining low CPAP fluctuations throughout the breath cycle utilizing a frustrum-shaped air channel to accelerate air flow. In some embodiments, a manometer is provided for monitoring pressure and/or a pressure relief valve is provided as a safety measure against overpressure delivered to a patient. In some embodiments, the device is disposable for one-time or single patient use.

18 Claims, 19 Drawing Sheets

Related U.S. Application Data continuation-in-part of application No. 13/592,634, filed on Aug. 23, 2012, now Pat. No. 9,370,635.

(52) U.S. Cl.
CPC ........ *A61M 16/06* (2013.01); *A61M 16/0816* (2013.01); *A61M 16/0858* (2014.02); *A61M 16/127* (2014.02); *A61M 16/209* (2014.02); *A61M 2016/0027* (2013.01); *A61M 2016/003* (2013.01)

(58) Field of Classification Search
CPC ............ A61M 16/0858; A61M 16/127; A61M 16/209; A61M 2016/0027; A61M 2016/003; A61M 16/0875; A61M 39/00; A61M 2206/00
USPC ........................................ 128/200.18, 204.25
See application file for complete search history.

(56) References Cited

U.S. PATENT DOCUMENTS

| | | |
|---|---|---|
| 5,036,847 A | 8/1991 | Boussignac |
| 5,193,532 A | 3/1993 | Moa et al. |
| 5,538,002 A | 7/1996 | Boussignac et al. |
| 6,273,087 B1 | 8/2001 | Boussignac et al. |
| 6,516,801 B2 | 2/2003 | Boussignac |
| 6,761,172 B2 | 7/2004 | Boussignac et al. |
| 6,814,075 B2 | 11/2004 | Boussignac |
| 7,331,344 B2 | 2/2008 | Foster et al. |
| 7,905,229 B2 | 3/2011 | Giroux et al. |
| 8,561,609 B2 | 10/2013 | Donovan et al. |
| 8,950,400 B2 | 2/2015 | Enk |
| 9,370,635 B2 | 6/2016 | Ratner |
| 11,383,054 B2 * | 7/2022 | Ratner ............... A61M 16/0816 |
| 2003/0116163 A1 * | 6/2003 | Wood ................. A61M 16/0666 128/207.18 |
| 2004/0154617 A1 * | 8/2004 | Enk ........................ A61M 16/08 128/203.12 |
| 2005/0066976 A1 | 3/2005 | Wondka |
| 2007/0056587 A1 | 3/2007 | Travan |
| 2008/0054099 A1 * | 3/2008 | Giroux .................. B05B 7/2429 96/4 |
| 2008/0230053 A1 * | 9/2008 | Kraft ..................... B05B 7/0892 128/200.14 |
| 2009/0044807 A1 | 2/2009 | Boussignac |
| 2009/0234325 A1 | 9/2009 | Rozenberg et al. |
| 2010/0252041 A1 | 10/2010 | Kapust et al. |
| 2010/0252044 A1 | 10/2010 | Daquette |
| 2011/0088696 A1 | 4/2011 | Ratner |

* cited by examiner

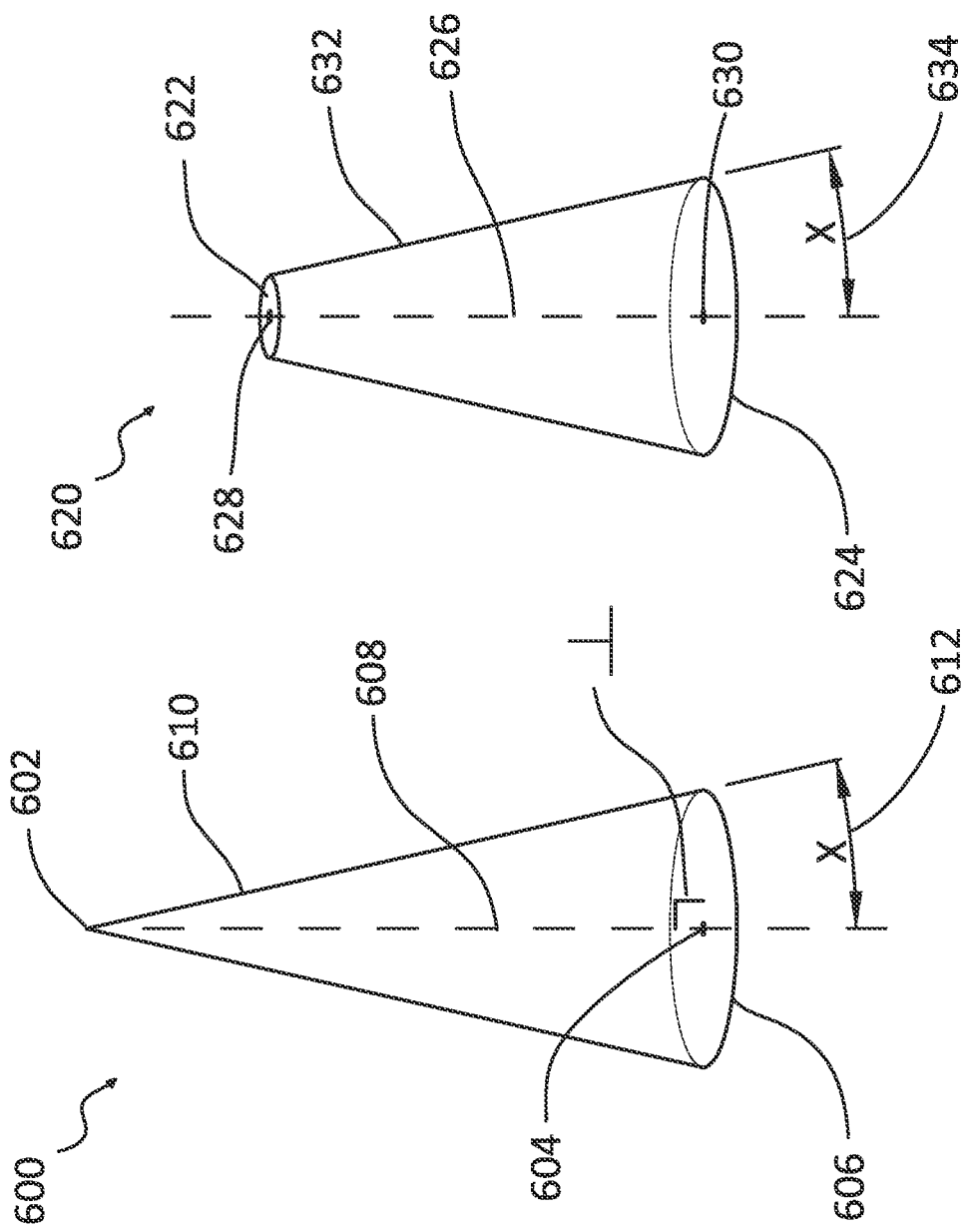

| TABLE 1: PATIENT END OPENING SIZE VS. STATIC PRESSURE ||||||
|---|---|---|---|---|---|
| WALL TYPE | PATIENT END DIAMETER MM | ANGLE OF FRUSTUM WALL | JET ORIFICE DIA. MM | GAS INPUT LPM | STATIC PRESSURE Cm H2O |
| STRAIGHT TUBE | 11.9 | 0 | 0.58 | 12 | 8.5 |
| STRAIGHT TUBE | 12.9 | 0 | 0.58 | 12 | 7.5 |
| STRAIGHT TUBE | 15.8 | 0 | 0.58 | 12 | 5.0 |

FIG. 13

| TABLE 2: PATIENT END OPENING SIZE VS. PRESSURE FLUCTUATION ||
|---|---|
| PATIENT END DIAMETER MM | PRESSURE FLUCTUATION Cm H2O |
| 10.2 | 2.8 |
| 11.0 | 1.5 |
| 12.0 | 1.2 |
| 12.8 | 1.0 |

FIG. 14

| TABLE 3: STEADY CROSS-SECTION WALLS (TUBES) VS. FRUSTUM-SHAPED WALLS OF SAME TYPE | | | | | | | | |
|---|---|---|---|---|---|---|---|---|
| WALL TYPE | PATIENT END OPENING CROSS SECTIONAL AREA SQ MM | WALL ANGLE DEGREES | JET ORIFICE DIAMETER MM | ORIFICE DISTANCE TO PATIENT END OPENING MM | CENTRAL AXIS LENGTH MM | GAS INPUT LPM | STATIC PRESSURE Cm H2O | PRESSURE FLUCTUATION Cm H2O |
| CONICAL FRUSTUM | 95 | 4 | 0.65 | 47 | 47 | 13 | 9.5 | 2.0 |
| CYLINDRICAL STRAIGHT TUBE | 95 | 0 | 0.65 | 47 | 47 | 13 | 11.5 | 7.0 |
| SQUARE FRUSTUM | 95 | 3.5* | 0.65 | 47 | 47 | 13 | 9.8 | 3.0 |
| SQUARE STRAIGHT TUBE | 95 | 0* | 0.65 | 47 | 47 | 13 | 11.5 | 5.5 |
| OCTAGONAL FRUSTUM | 95 | 3.8* | 0.65 | 47 | 47 | 13 | 9.5 | 2.0 |
| OCTAGONAL STRAIGHT TUBE | 95 | 0* | 0.65 | 47 | 47 | 13 | 11.5 | 4.8 |
| *ANGLE MEASURED TO THE CENTER OF THE SIDE AS IN FIGURE 12 | | | | | | | | |

FIG. 15

| TABLE 4: PRESSURE CHARACTERISTICS THROUGH RANGE OF FRUSTUM ANGLES | | | | | | |
|---|---|---|---|---|---|---|
| PATIENT END DIAMETER MM | ORIFICE DISTANCE TO PATIENT END OPENING MM | FRUSTUM ANGLE X | JET ORIFICE DIAMETER MM | GAS INPUT LPM | STATIC PRESSURE Cm H2O | PRESSURE FLUCTUATION Cm H2O |
| 11 | 47 | 0 | 0.65 | 13 | 11.5 | 7.0 |
| 11 | 47 | 2 | 0.65 | 13 | 10.0 | 2.5 |
| 11 | 47 | 3 | 0.65 | 13 | 9.5 | 2.3 |
| 11 | 47 | 4 | 0.65 | 13 | 9.5 | 1.5 |
| 11 | 47 | 5 | 0.65 | 13 | 9.5 | 2.3 |
| 11 | 47 | 6 | 0.65 | 13 | 10.0 | 3.0 |
| 11 | 47 | 7 | 0.65 | 13 | 10.0 | 3.0 |
| 11 | 47 | 8 | 0.65 | 13 | 11.0 | 3.0* |
| 11 | 47 | 9 | 0.65 | 13 | 10.5 | 3.0* |
| * SLIGHT BUFFETING | | | | | | |

FIG. 16

| TABLE 5: TESTS PERFORMED USING 0.58 ORIFICE ||||||||
|---|---|---|---|---|---|---|---|
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
| STRAIGHT TUBE | 11.9 | 0 | 56.5 | 0.58 | 12 | 8.5 | 4.0 |
| STRAIGHT TUBE | 12.9 | 0 | 50.0 | 0.58 | 12 | 7.5 | 3.0 |
| STRAIGHT TUBE | 12.9 | 0 | 81.0 | 0.58 | 12 | 7.5 | 2.5 |
| STRAIGHT TUBE | 15.8 | 0 | 72.5 | 0.58 | 12 | 5.0 | 1.5 |
| CONICAL FRUSTUM | 11.0 | 4 | 27.0 | 0.58 | 12 | 9.0 | 4.5 |
| CONICAL FRUSTUM | 11.0 | 4 | 37.0 | 0.58 | 12 | 9.5 | 3.0 |
| CONICAL FRUSTUM | 11.0 | 4 | 47.0 | 0.58 | 12 | 9.3 | 3.0 |
| CONICAL FRUSTUM | 11.0 | 4 | 57.0 | 0.58 | 12 | 8.0 | 1.0 |
| CONICAL FRUSTUM | 11.0 | 4 | 67.0 | 0.58 | 12 | 7.5 | 2.5 |
| CONICAL FRUSTUM | 15.8 | 4 | 27.0 | 0.58 | 12 | 4.5 | 0.8 |
| CONICAL FRUSTUM | 15.8 | 4 | 37.0 | 0.58 | 12 | 4.5 | 1.0 |
| CONICAL FRUSTUM | 15.8 | 4 | 47.0 | 0.58 | 12 | 4.8 | 2.3 |
| CONICAL FRUSTUM | 15.8 | 4 | 57.0 | 0.58 | 12 | 4.8 | 1.5 |
| CONICAL FRUSTUM | 15.8 | 4 | 67.0 | 0.58 | 12 | 4.3 | 1.5 |
| CONICAL FRUSTUM | 11.8 | 4 | 77.5 | 0.58 | 12 | 5.5 | 0.5 |

FIG. 17

| TABLE 6: TESTS PERFORMED USING 0.65 ORIFICE ||||||||
|---|---|---|---|---|---|---|---|
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
| STRAIGHT TUBE | 11.9 | 0 | 56.5 | 0.65 | 13 | 9.5 | 3.5 |
| STRAIGHT TUBE | 12.9 | 0 | 50.0 | 0.65 | 13 | 8.0 | 3.0 |
| STRAIGHT TUBE | 12.9 | 0 | 81.0 | 0.65 | 13 | 8.0 | 3.0 |
| STRAIGHT TUBE | 15.8 | 0 | 72.5 | 0.65 | 13 | 5.0 | 1.5 |
| CONICAL FRUSTUM | 11.0 | 4 | 27.0 | 0.65 | 13 | 9.5 | 4.0 |
| CONICAL FRUSTUM | 11.0 | 4 | 37.0 | 0.65 | 13 | 10.0 | 2.0 |
| CONICAL FRUSTUM | 11.0 | 4 | 47.0 | 0.65 | 13 | 9.5 | 1.5 |
| CONICAL FRUSTUM | 11.0 | 4 | 57.0 | 0.65 | 13 | 8.5 | 2.5 |
| CONICAL FRUSTUM | 11.0 | 4 | 67.0 | 0.65 | 13 | 8.0 | 2.5 |
| CONICAL FRUSTUM | 15.8 | 4 | 27.0 | 0.65 | 13 | 5.3 | 0.5 |
| CONICAL FRUSTUM | 15.8 | 4 | 37.0 | 0.65 | 13 | 4.8 | 1.0 |
| CONICAL FRUSTUM | 15.8 | 4 | 47.0 | 0.65 | 13 | 5.0 | 1.5 |
| CONICAL FRUSTUM | 15.8 | 4 | 57.0 | 0.65 | 13 | 5.0 | 2.0 |
| CONICAL FRUSTUM | 15.8 | 4 | 67.0 | 0.65 | 13 | 4.8 | 1.8 |
| CONICAL FRUSTUM | 11.8 | 4 | 77.5 | 0.65 | 13 | 6.5 | 1.5 |

FIG. 18

| TABLE 7: TESTS PERFORMED USING 0.79 ORIFICE | | | | | | | |
|---|---|---|---|---|---|---|---|
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
| STRAIGHT TUBE | 11.9 | 0 | 56.5 | 0.79 | 18 | 13.5 | 5.0 |
| STRAIGHT TUBE | 12.9 | 0 | 50.0 | 0.79 | 18 | 11.0 | 4.0 |
| STRAIGHT TUBE | 12.9 | 0 | 81.0 | 0.79 | 18 | 11.0 | 3.0 |
| STRAIGHT TUBE | 15.8 | 0 | 72.5 | 0.79 | 18 | 7.0 | 2.5 |
| CONICAL FRUSTUM | 11.0 | 4 | 27.0 | 0.79 | 18 | 13.5 | 5.0 |
| CONICAL FRUSTUM | 11.0 | 4 | 37.0 | 0.79 | 18 | 14.0 | 3.5 |
| CONICAL FRUSTUM | 11.0 | 4 | 47.0 | 0.79 | 18 | 13.0 | 1.5 |
| CONICAL FRUSTUM | 11.0 | 4 | 57.0 | 0.79 | 18 | 11.5 | 1.5 |
| CONICAL FRUSTUM | 11.0 | 4 | 67.0 | 0.79 | 18 | 11.0 | 2.0 |
| CONICAL FRUSTUM | 15.8 | 4 | 27.0 | 0.79 | 18 | 6.8 | 0.8 |
| CONICAL FRUSTUM | 15.8 | 4 | 37.0 | 0.79 | 18 | 6.8 | 2.0 |
| CONICAL FRUSTUM | 15.8 | 4 | 47.0 | 0.79 | 18 | 7.0 | 2.0 |
| CONICAL FRUSTUM | 15.8 | 4 | 57.0 | 0.79 | 18 | 6.8 | 2.5 |
| CONICAL FRUSTUM | 15.8 | 4 | 67.0 | 0.79 | 18 | 6.5 | 1.5 |
| CONICAL FRUSTUM | 11.8 | 4 | 77.5 | 0.79 | 18 | 9 | 2.5 |

FIG. 19

| TABLE 8: STATIC PERFORMANCE COMPARISON OF COMMONLY USED CPAP DEVICES | | |
|---|---|---|
| DEVICE | GAS INPUT LPM | STATIC PRESSURE Cm H2O |
| BOUSSIGNAC CPAP DEVICE | 25.0 | 6.8* |
| MERCURY FLOW SAFE CPAP DEVICE | 25.0 | 8.9 |
| APPLICANT'S INVENTION | 12.5 | 8.9 |
| BOUSSIGNAC CPAP DEVICE | 29.5 | 10.0 |
| MERCURY FLOW SAFE CPAP DEVICE | 25.9 | 10.0 |
| APPLICANT'S INVENTION | 13.6 | 10.0 |
| *BOUSSIGNAC DEVICE TESTED DID NOT MEET ADVERTISED SPECIFICATION | | |

FIG. 20

| TABLE 9: DYNAMIC PERFORMANCE COMPARISON OF COMMONLY USED CPAP DEVICES | | | |
|---|---|---|---|
| DEVICE | GAS INPUT LPM | STATIC PRESSURE Cm H2O | PRESSURE FLUCTUATION Cm H2O |
| BOUSSIGNAC CPAP DEVICE | 29.5 | 10.0 | 3.5 |
| MERCURY FLOW SAFE CPAP DEVICE | 25.9 | 10.0 | 3.8 |
| APPLICANT'S INVENTION | 13.6 | 10.0 | 1.7 |

FIG. 21

OPTIMIZED BREATHING ASSISTANCE DEVICE

CROSS-REFERENCE TO RELATED APPLICATION

This application is a continuation of U.S. patent application Ser. No. 15/161,610, filed May 23, 2016, which, in turn, is a continuation of U.S. patent application Ser. No. 13/592,634, filed Aug. 23, 2012, the disclosure of which is hereby incorporated by reference.

FIELD

The present invention relates to the field of breathing assistance devices.

BACKGROUND

Breathing aids or breathing assistance devices are well known in the art. Numerous devices have been disclosed which are designed to assist a patient who is having difficulty breathing. These devices often supply supplemental oxygen at a concentration higher than that in the atmosphere, and often under pressure, as a means of promoting improved respiration and/or improved oxygen absorption. Further, numerous breathing assistance devices which are designed to provide a continuous positive airway pressure (CPAP) have likewise been disclosed.

For example, U.S. Pat. No. 5,036,847, by Boussignac et al., discloses a breathing aid comprising a tubular main channel through which respiration occurs, with one end open to the atmosphere and at least one additional auxiliary channel opening into the main channel through which supplemental pressurized respirable gas (e.g. oxygen) is provided to the patient. The device produces a continuous positive airway pressure (CPAP). The invention of U.S. Pat. No. 5,036,847 also comprises a deflection face as a means to deflect the jet(s) of respirable gas exiting the auxiliary channel(s) towards the center of the main channel so that the jet(s) of respirable gas does not directly strike the patient's mucous membranes. Further, the disclosure also provides for an additional channel which opens into the distal (patient) end of the tube and which may be connected to a pressure measurement device as well as a safety pressure relief device (comprising perforations through the main tube in conjunction with a safety sleeve) to relieve pressure within the main tube in the event that the internal pressure becomes too high.

U.S. Pat. Nos. 5,538,002, 6,273,087, 6,363,935, 6,516,801, 6,761,172, and 6,814,075, as well as U.S. Patent Application No. 2009/0044807 A1, all by Boussignac (et al.), each likewise disclose similar inventions with various additional features. Many of these provide for a calibrated pressure relief valve in the proximal region of the main tube to relieve pressure in the main channel in the case of overpressure. Most of these require that the auxiliary channel(s) open into the main tube near ("close to," "in proximity of," "in the vicinity of") the distal (i.e. patient) end of the device.

As another example, U.S. Pat. No. 5,193,532 by Moa et al., discloses a breathing assistance device which produces a continuous positive airway pressure by means of an ejector action due to the influx of supplemental respirable gas into a breathing channel through an inlet channel. This device, like the Boussignac devices referred to above, also exhibits a branch channel open to the atmosphere and is therefore not a closed circuit, ventilator type CPAP system. Further, in this device the breathing channel (first branch channel) and the exhaust channel (second branch channel) are not linearly aligned but rather form an angle of 30 to 50 degrees with one another.

U.S. Pat. No. 7,331,344, by Foster et al., discloses yet another example of a "breathing device" wherein supplemental respirable gas is provided into a breathing channel through an inlet channel. As in the above examples, the exhaust channel in this invention is open to the atmosphere. And here, once again, the breathing channel and exhaust channel are not collinear but rather form an oblique angle with one another. The inlet channel is laterally offset from the breathing channel so as to introduce supplemental respirable gas in such a manner that a "bypass" occurs, whereby some portion of the supplemental respirable gas goes directly to the exhaust channel. According to the author, "It has been recognized that the phenomena of jet bypass, whereby a proportion of the fresh gas supplied to the patient passes directly out of the exhaust tube is crucial in giving the low added work of breathing." Col. 1, Lines 38-41.

U.S. Pat Application No. 20110088696, by Ratner, discloses a disposable breathing assistance device with manometer for monitoring the pressure within the device, a safety pressure relief valve and a specialized supplementary respirable gas inlet combined with a specialized main channel which provides improved pressure characteristics.

Each of the above-described devices provide an exhaust channel open to the atmosphere yet provide a continuous positive airway pressure at the user end of the device. The use of continuous positive airway pressure both forces gas into the lungs during inhalation and forces the patient to exhale against pressurized gas during exhalation which may prevent the alveoli from collapsing. It has been found that in many cases, the use of such a CPAP device is of great assistance to patients experiencing breathing difficulties.

SUMMARY

In one embodiment, a breathing assistance device is disclosed including a body that has an interior wall that defines an interior space. The interior wall has a narrow end and a wide end and has a cross-sectional area that is continuously smaller from the wide end to the narrow end. A patient connector is interfaced to the narrow end. The patient connector is adapted to be engaged directly with a patient's breathing tract or adapted to be engaged indirectly with the patient's breathing tract. A gas jet has a jet orifice that is aimed into the wide end of the interior wall. The gas jet is adapted to be supplied with the gas from a source of the gas under pressure, directing the gas through said interior space substantially along a central, lengthwise axis of the interior space towards the patient connector. The interior wall is continuous between the narrow end and the wide end.

In another embodiment, a breathing assistance device is disclosed including a body that has an interior wall that is continuous without breaks. The interior wall has a narrow end and a wide end. A patient connector is interfaced to the narrow end of the interior wall. The interior wall has a central, longitudinal axis passing from a center of the narrow end and a center of the wide end. The interior wall forms a linear angle with the central, longitudinal axis of greater than 0 degrees and less than 8 degrees. There is at least one opening to an atmosphere fluidly interfaced to the breathing assistance device and in fluid communications with the wide end, thereby allowing exhalation gases to exit to the atmosphere. A gas jet is adapted to be supplied with a gas from a pressurized gas source, the gas jet directing the gas into the wide end of the wide end aimed towards the narrow end. A cross-sectional area of the body decreases linearly from the wide end to the narrow end.

In another embodiment, a method of increasing airflow of a gas from a breathing device is disclosed. There is a certain gas volume input to the breathing device and the breathing device has a includes expelling the gas from a gas jet into a wide end of the body of the breathing device and aimed toward a narrow end of the body. A cross-sectional area of the interior walls of the body of the breathing device decreasing linearly from the wide end of the body to the narrow end of the body. This provides flow of the gas from the narrow end of the body to a patient through a direct or indirect patient interface. The interior walls of the body are continuous and without breaks between the wide end and the narrow end.

There are numerous disadvantages to previously disclosed inventions.

First, applicant has discovered that many previously disclosed devices do not use supplementary respirable gas as efficiently as is both possible and desirable. CPAP is often applied in situations where a limited supplementary respirable gas supply is available; for example where portable oxygen containers are used on site in emergency situations. The length of time a CPAP device can be supplied using a given portable supplementary respirable gas tank is dependent upon the rate at which the supplementary respirable gas is used. Therefore devices that unnecessarily use supplementary respirable gas at faster rates are clearly less desirable in such situations. Whereas the ability to generate the same effective CPAP using a reduced quantity of supplementary respirable gas is desirable since it extends the length of time a given supplementary respirable gas supply can serve effectively. Additionally, there is an advantage to conserving supplementary respirable gas in general as a means of cost containment, even in situations where the supplementary respirable gas supply is not so strictly limited as it is in the examples above. The applicant's design provides the same effective CPAP as many previously disclosed devices while dramatically reducing the supplementary respirable gas requirements to accomplish this effect.

A second disadvantage to previously disclosed devices is that typically the CPAP pressure inside currently commonly used CPAP systems will increase significantly during patient exhalation and decrease significantly during patient inhalation. In CPAP application, this type of pressure fluctuation is considered to be associated with an increased work of breathing, i.e. larger fluctuations of internal pressure making breathing more difficult for the patient whose breathing is already distressed. For this reason, there is an advantage in reducing the amplitude of this type of pressure fluctuation. Experimentation involving variation of multiple parameters was undertaken by applicant in order to optimize the function and achieve the desired effect. As a result, applicant's invention not only provides for effective CPAP with reduced supplementary gas requirements, but also addresses the fluctuation issue as well, and provides a stable, consistent CPAP pressure with minimal fluctuation throughout the breathing cycle. These are 2 very desirable qualities in a breathing assistance device.

Additionally, the disclosed device provides for the attachment of a manometer for internal pressure measurement and may optionally comprise a calibrated pressure relief valve for added safety against overpressure and its dangers to the patient. Further, the entire device may be made to be completely disposable for one time or single patient use.

BRIEF DESCRIPTION OF THE DRAWINGS

FIGS. 6A, 6B, and 6C compare a right circular cone, a right circular conic frustum, and a cylindrical tube and illustrates the measurement of the angle of the frustum wall in relation to the central axis.

FIG. 13—Table 1 illustrates the relationship between Static Pressure and Patient End Opening Size.

FIG. 14—Table 2 illustrates the relationship between Pressure Fluctuation and Patient End Opening Size.

FIG. 15—Table 3 compares Tubular structures with Frustum-shaped Walls.

FIG. 16—Table 4 illustrates the relationship between Frustum Wall Angle and Pressure Characteristics.

FIG. 17—Table 5 tabulates examples of experimental results obtained using a 0.58 mm diameter jet orifice.

FIG. 18—Table 6 tabulates examples of experimental results obtained using a 0.65 mm diameter jet orifice.

FIG. 19—Table 7 tabulates examples of experimental results obtained using a 0.79 mm diameter jet orifice.

FIG. 20—Table 8 compares Static Pressure produced vs. LPM supplementary gas flow in applicant's invention and 2 prior art devices.

FIG. 21—Table 9 compares Pressure Fluctuation in applicant's invention with 2 prior art devices.

(5) REFERENCE NUMERALS IN DRAWINGS

Figure 1:
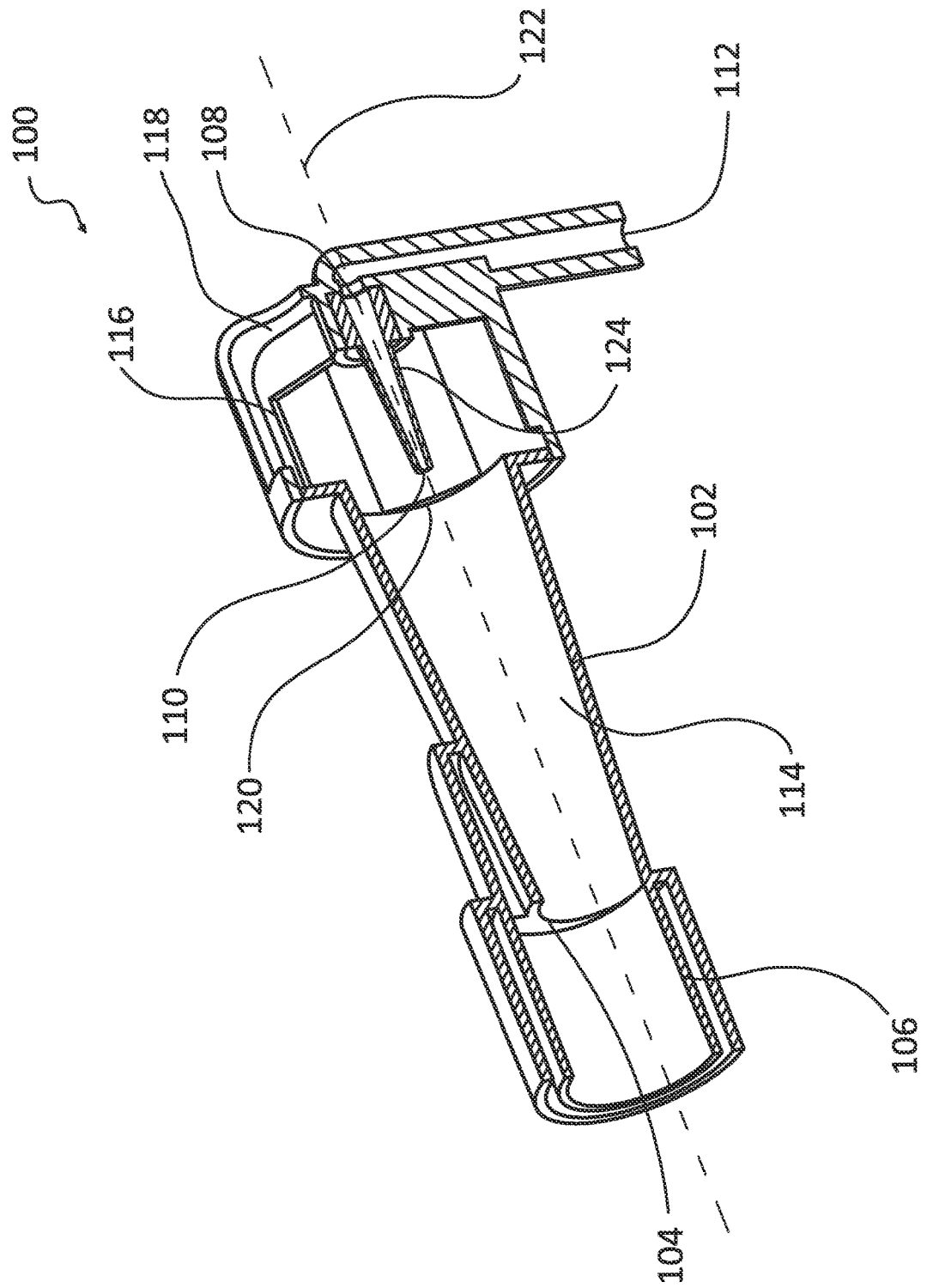
FIG. 1 shows an isometric section view of an example of a breathing assistance device according to the present invention

100 Breathing assistance device
102 Interior wall
104 Narrow End
106 Connector
108 Jet
110 Jet Orifice
112 Gas Input Port
114 Interior Space
116 Atmospheric Opening
118 Endcap 120 Wide End
122 Central Axis of Frustum-Shaped Wall
124 Frustum-Shaped Wall of Jet
300 Test Fixture
302 Linear Slide Controlled by Stepper Motor
304 3-Liter Syringe
306 Computer
308 Breathing Assistance Device
310 Pressure Gauge
312 Syringe/Breathing Assistance Device Junction
314 Supplementary Gas Tank
316 Flow Meter
318 Connective Tubing
400 Regular Square Pyramid
420 Frustum of Regular Square Pyramid
422 Narrow End/Top Face of Frustum
424 Wide End/Bottom Face of Frustum
426 Central Axis of Frustum
428 Geometric Center of Square Top Face of Frustum
430 Geometric Center of Square Bottom Face of Frustum
440 Square Tube
442 Length of Square Tube
444 Central Axis of Square Tube
500 Regular Octagonal Pyramid
520 Frustum of Regular Octagonal Pyramid
522 Narrow End/Top Face of Frustum
524 Wide End/Bottom Face of Frustum
526 Central Axis of Frustum
528 Geometric Center of Octagonal Top Face of Frustum
530 Geometric Center of Octagonal Bottom Face of Frustum
540 Octagonal Tube
542 Length of Octagonal Tube
544 Central Axis of Octagonal Tube
600 Right Circular Cone
602 Vertex of Cone
604 Center of Base of Cone
606 Base of Cone
608 Central Axis of Cone
610 Wall of Cone
612 Angle Between Wall of Cone and Central Axis
620 Frustum of Right Circular Cone
622 Narrow End/Top Face of Frustum
624 Wide End/Bottom Face of Frustum
626 Central Axis of Frustum
628 Geometric Center of Top Face of Frustum
630 Geometric Center of Bottom Face of Frustum
632 Wall of Frustum
634 Angle between Wall of Frustum and Central Axis
640 Cylindrical Tube
642 Length of Cylindrical Tube
644 Central Axis of Cylindrical Tube
700 An example of a breathing assistance device according to the present invention
with manometer and pressure relief valve.
702 Manometer
704 Pressure Relief Valve
706 Manometer Port
708 Connector
710 Pressure Release Vent
712 Atmospheric Opening
714 Endcap
716 Gas Input Port
802 Pressure Measurement Channel
804 Through hole
806 Frustum-shaped Wall
808 Pressure Relief Valve Housing
810 Endcap
812 Ball of the Pressure Relief Valve
814 Spring of Pop-off Safety Relief Valve
816 Interior Space
818 Jet
820 Patient End Opening
822 Jet Orifice
1000 Irregular Heptagonal Pyramid
1002 Vertex of Pyramid
1004 Centroid of Base of Pyramid
1006 Base of Pyramid
1008 Central Axis of Pyramid
1020 Frustum of Irregular Heptagonal Pyramid
1022 Central Axis of Frustum
1024 Narrow End/Top Face of Frustum
1026 Wide End/Bottom Face of Frustum
1028 Centroid of Heptagonal Top Face of Frustum
1030 Centroid of Heptagonal Bottom Face of Frustum
1040 Irregular Heptagonal Tube
1042 Top Face of Irregular Heptagonal Tube
1044 Bottom Face of Irregular Heptagonal Tube
1046 Side Face of Irregular Heptagonal Tube
1048 Central Axis of Irregular Heptagonal Tube
1100 Right Circular Cone
1102 Central Axis of Cone
1104 Bottom Face of Cone
1106 Wall of Cone
1108 Angle Between Wall of Cone and Central Axis
1120 Angled Frustum of Cone
1122 Top Face of Angled Frustum
1124 Bottom Face of Angled Frustum
1126 Central Axis
1128 Circular Cross-Section Perpendicular to Central Axis of Cone and Tangent to Top Face of Cone Portion
1130 Circular Cross-Section Perpendicular to Central Axis of Cone and Tangent to Bottom Face of Cone Portion
1132 Top Portion
1134 Middle Portion
1136 Bottom Portion
1140 Portion of Cone
1142 Circular Cross-Section Perpendicular to Central Axis of Cone and Tangent to Top Face of Cone Portion
1144 Circular Cross-Section Perpendicular to Central Axis of Cone and Tangent to Bottom Face of Cone Portion
1146 Top Portion
1148 Middle Portion
1150 Bottom Portion
1152 Top Face of Cone Portion
1154 Bottom Face of Cone Portion
1200 Frustum of Regular Square Pyramid
1202 Square Top Face of Frustum
1204 Center of Top Face
1206 Square Bottom Face of Frustum
1208 Center of Bottom Face
1210 Central Axis of Frustum
1212 Side Face of Frustum
1214 Line Drawn Down Center of Side Face of Frustum
1216 Angle Between Center of Side Face and Central Axis
1218 Edge Between Side Faces
1220 Angle Between Edge and Central Axis

DETAILED DESCRIPTION

Figure 2:
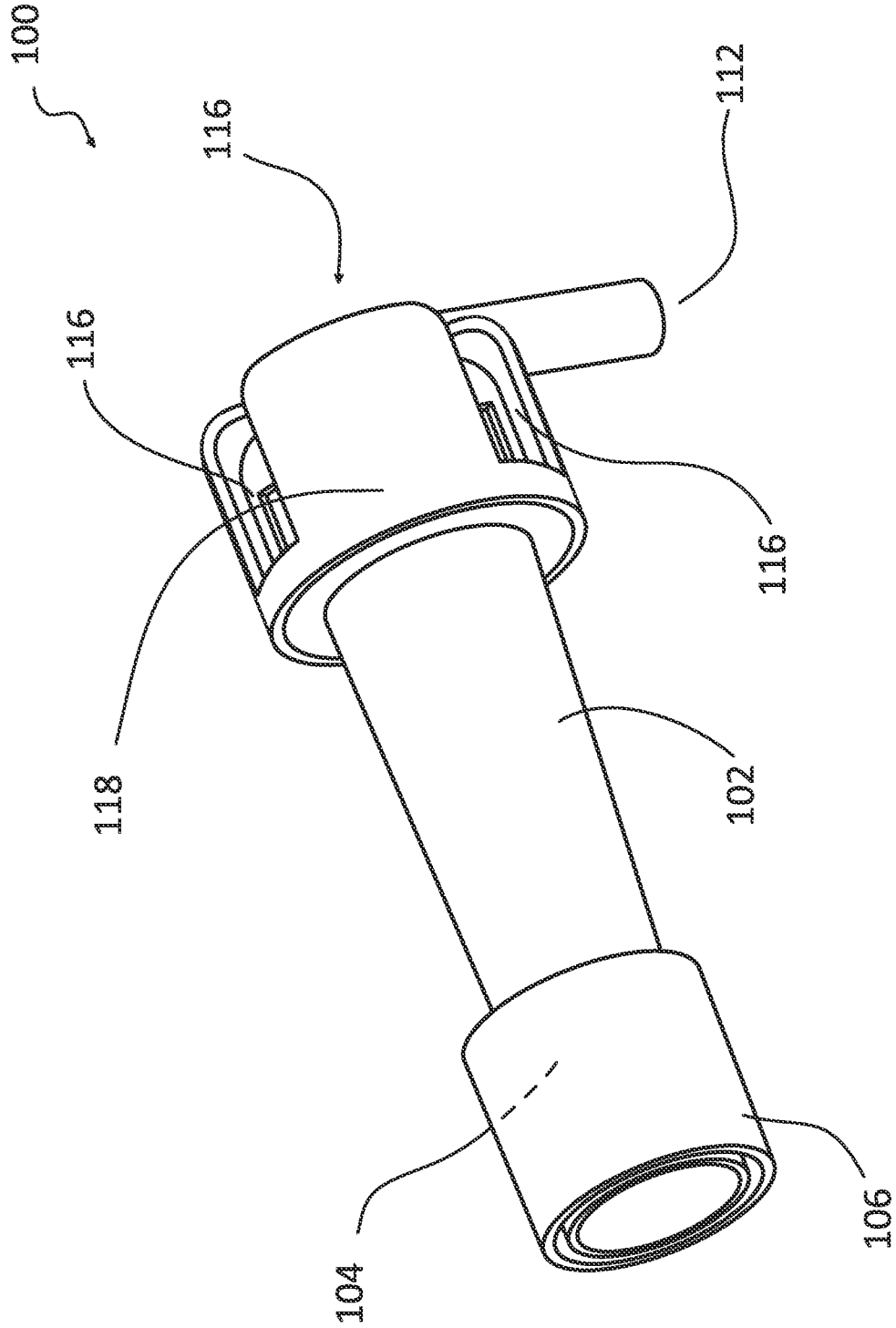
FIG. 2 shows an isometric view of an example of a breathing assistance device according to the present invention.

The breathing assistance device 100 is shown in FIG. 1 for a cross-section FIG. 2 for an isometric view. The breathing assistance device 100 generally comprises a body that has interior walls 102 that have a cross-sectional area that continuously narrows from a wide end 120 to a narrow end 104 of the body, e.g., a frustrum-shape. In such, the interior walls 102 are without interruption (e.g., are continuous). The interior wall 102 defines the interior space 114. The narrow end 104 of the interior walls 102 is the patient end and has a patient connector 106. Exhaled gas will enter the patient connector 106 from the patient end during exhalation of the patient. The patient connector 106 is adapted to be engaged directly with a patient's breathing tract (e.g., by formation into an endotracheal tube) or adapted to be engaged indirectly with a patient's breathing tract (e.g., via connection to a mask). The breathing assistance device 100 further comprises a gas jet 124 that is aimed into the wide end 120 of the body. In use, the gas jet 124 directs a gas (e.g., a supplementary respirable gas such as compressed air or oxygen) from a gas source, such as an oxygen tank, through the interior space 114 towards the patient connector 106. Associated with the gas jet 124, there are atmospheric openings 116 to the atmosphere which allow fluid communication of gases between the interior space and the atmosphere, e.g., during exhalation. The breathing assistance device further comprises a gas input port 112 interfaced to the gas jet 124 for connection to the source of gas, such as concentrated oxygen. The gas jet 124 is located at the wide end 120 of the body and the interior walls 102 have a cross-sectional area that continuously narrows from a wide end 120 where the gas jet 124 is located, to a narrow end 104 of the body. In some embodiments, it is preferred that the interior walls 102 are continuous, without interruption.

In use, the gas jet 124 sends the gas down the interior space 114 from the wide end 120 to the narrow end 104 and the continuously narrowing cross-sectional area of the interior space 114 creates an increase in gas pressure, particularly at the narrow end 104, near the patient connector 106 and beyond, into the patient's airway. Upon inhalation, the patient breathes in the gas that enters the interior space though the gas jet 124 as well as atmospheric air that is drawn into the interior space though the atmospheric openings 116. Upon exhalation, the expired gases exit from the patient, through the patient connector 106, through the interior space 114, and finally exiting the device through the atmospheric openings 116.

By designing the breathing assistance device 100 with a selected angle of the interior walls 102 (e.g., the frustum-shaped interior wall) in relation to the central axis of the breathing assistance device 100, a selected cross-sectional shape of the interior walls 102, a selected size of the narrow end 104, a selected distance of the gas jet 124 from the narrow end 104, a selected position of the gas jet 124 in relation to the central axis, and a selected size of an orifice 110 of the gas jet 124 through which gas is injected, the breathing assistance device 100 is optimized to provide desirable pressure characteristics including:

1) Reducing an amount of gas required to achieve a given pressure at the patient end of the device compared to prior art devices;

and

2) Reducing the amplitudes of pressure fluctuations within the device throughout the breathing cycle as compared with pressure fluctuations within prior art devices, resulting in a desirable reduction in the patient's effort in breathing as compared to the effort in breathing required using prior art devices.

Figure 7:
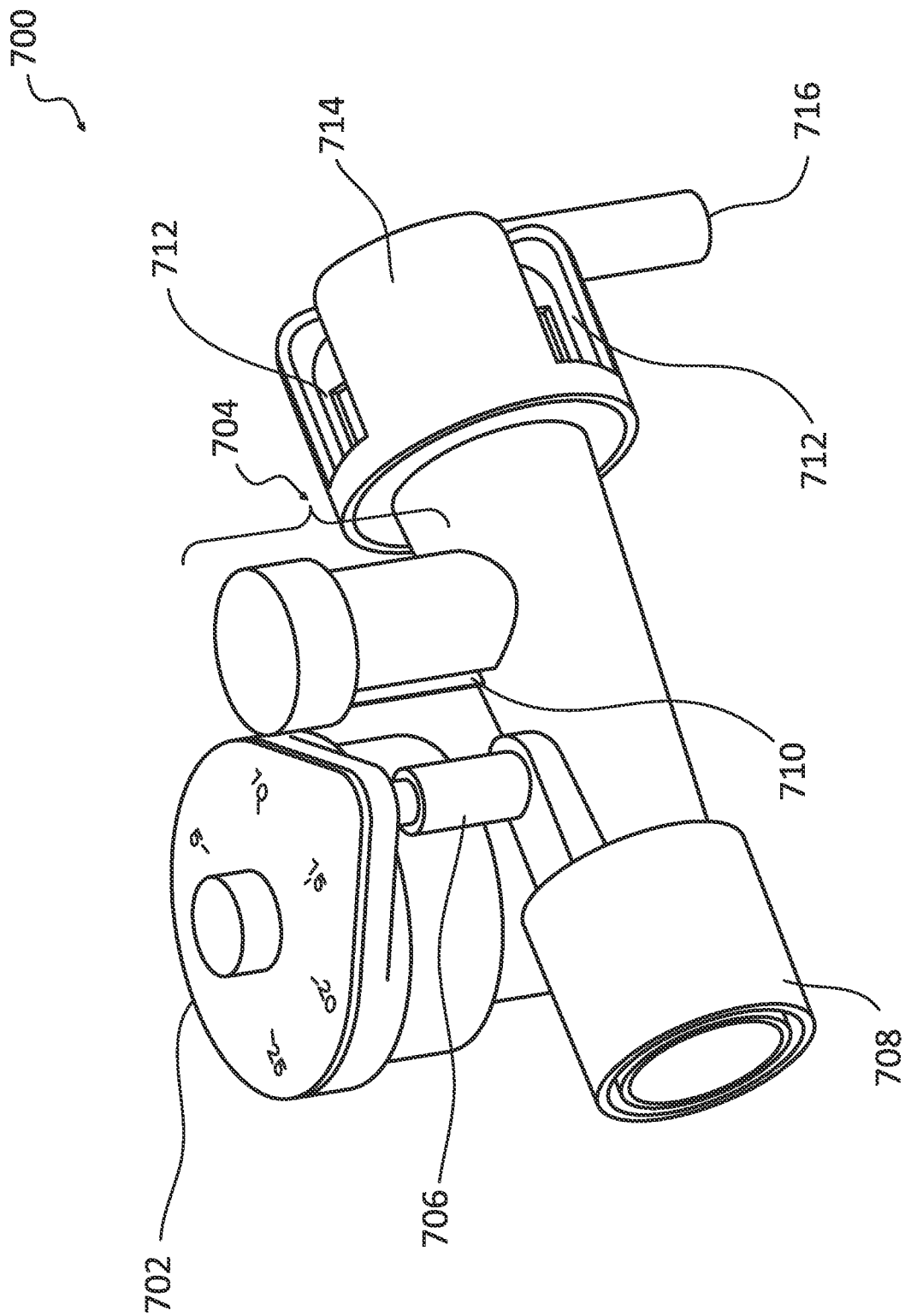
FIG. 7 shows an isometric view of an example of a breathing assistance device with manometer and pressure relief valve according to the present invention.
Figure 8:
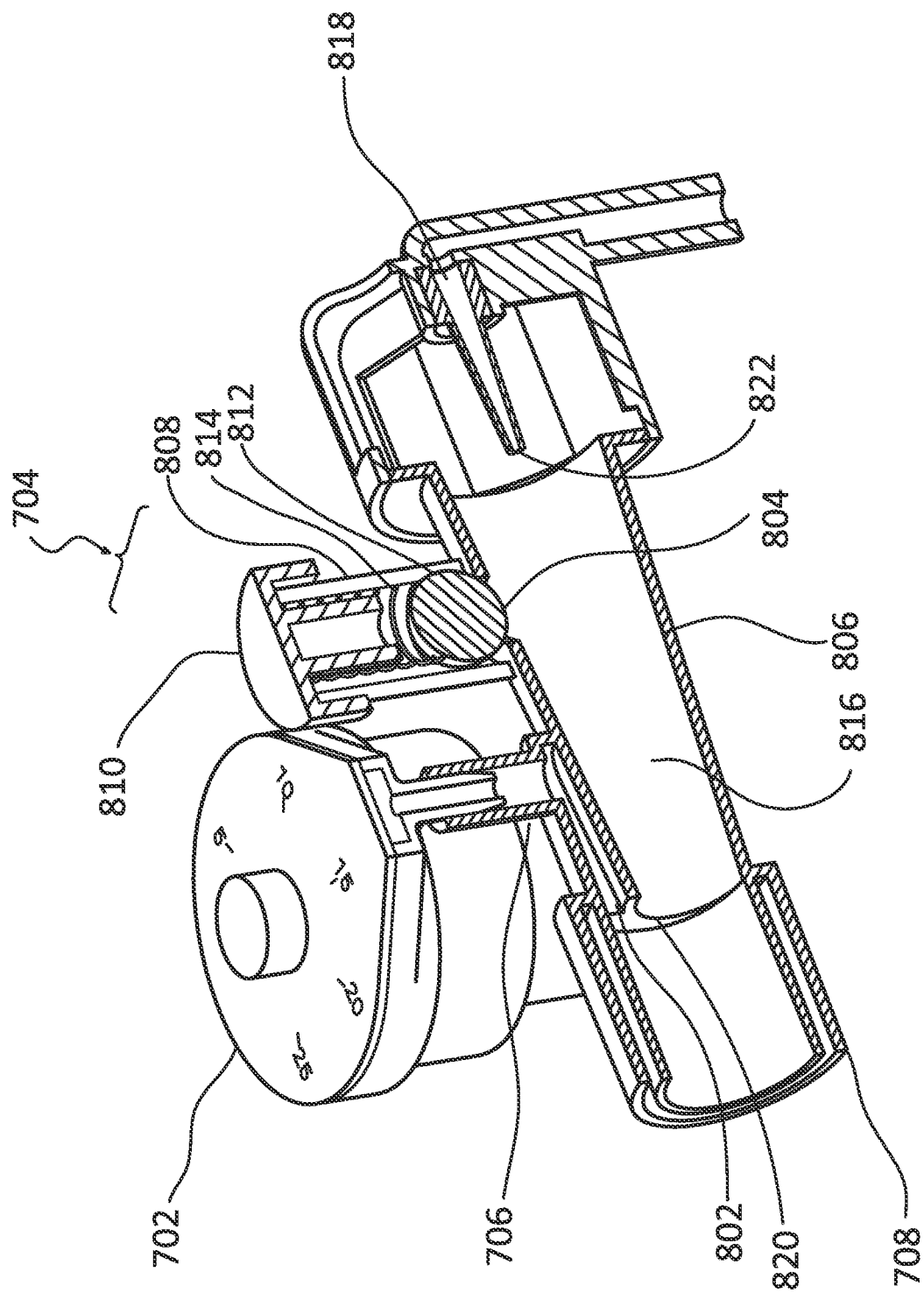
FIG. 8 shows an isometric section view of an example of a breathing assistance device with manometer and pressure relief valve according to the present invention.

In some embodiments, the breathing assistance device 100 includes a manometer 702 (see FIGS. 7 and 8). In such embodiments, the manometer 702 is interfaced to the interior space 114 through a pressure measurement channel 802 that interfaces directly with the patient connector 106 so as to measure the pressure within the interior space 114 and continuously provides an indication of this pressure. Note that the manometer 702 is purposely not interfaced directly to the interior walls 102 between the wide end 120 and the narrow end 104 for various reasons including providing a more accurate pressure reading and to maintain continuous interior walls 102 (without interruption). In some embodiments, the breathing assistance device 100 includes a pressure relief valve 704 for relieving excessive gas pressure from the interior space 114. The pressure relief valve 704 has a pressure relief through hole 804 that interrupts the interior walls 102. As the pressure relief through hole 804 is normally closed by a ball 812, in some such embodiments, the interior walls 102 remain continuous as the ball 812 normally occludes the pressure relief through hole 804 (unless excess gas pressure is present).

In order to optimize supplementary respirable gas utilization within a CPAP device, applicant undertook experimentation with various breathing aid prototypes of differing internal architectural designs. The basic design of each of the prototypes comprised a jet of respirable gas directed towards patient end openings that were set in different architectural surroundings in an attempt to optimize the gas flow through the opening, as well as the pressure characteristics around the opening, for CPAP purposes.

Figure 3:
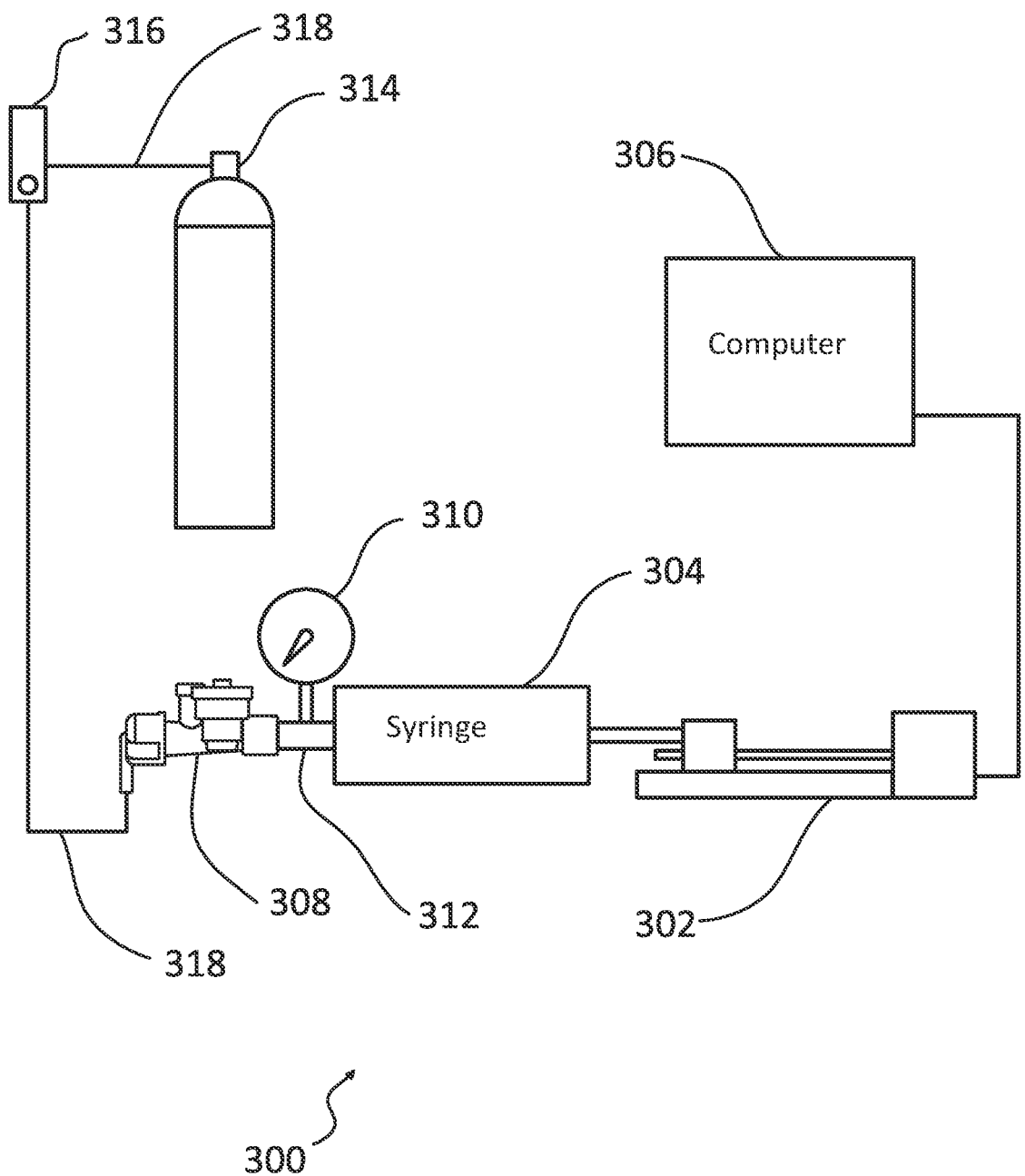
FIG. 3 shows a diagram of the test fixture.

Applicant created a test fixture to reproduce the dynamic breathing pattern of a distressed adult patient with a tidal volume of 1720 ml, an inspiratory time to expiratory time (I:E) ratio of 1:1, and a breath rate of 19 breaths per minute (BPM). Referring to FIG. 3, a representation of the test fixture 300 is shown. The test fixture utilizes a linear slide controlled by a stepper motor 302 to alternately pump air out of and draw air into a syringe 304 (e.g., 3-liter volume syringe). A computer 306 controls the stepper motor 302 to produce the desired respiration pattern. The syringe 304 is engaged with the patient connector 106 of the test breathing assistance device 308 to be tested. A pressure gauge 310 is interposed at the junction 312 between the syringe 304 and the patient connector 106 of the test breathing assistance device 308, allowing for constant immediate monitoring of the gas pressure at a point approximately 32 mm outside the patient connector 106 of the test breathing assistance device 308 being tested. This point might be equivalent to a point just inside a face mask and outside a patient's mouth of a typical use, or within the external end of an endotracheal tube, etc. depending upon the patient interface arrangement utilized. A supplementary gas tank 314 and an adjustable flow meter 316 are connected via tubing 318 to the gas input port 112 of the test breathing assistance device 308 to be tested.

Experimental prototypes were tested on this test fixture 300 in a static condition (i.e., stepper motor off and slide stationary, analogous to patient not breathing) and a dynamic condition (i.e., stepper motor on and continuously pumping syringe via slide, analogous to patient breathing). In the static condition, the static CPAP pressure generated was recorded in cm H2O for each LPM (liters per minute) gas input flow tested. In the dynamic condition, the peak high CPAP pressure was recorded during the exhale phase and the peak low CPAP pressure was recorded during the inhale phase in cm H2O for each LPM gas input flow tested. The pressure fluctuation (delta) is calculated by subtracting the peak low pressure from the peak high pressure.

In attempting to optimize the function of the breathing assistance device, certain limitations are immediately placed upon the preferable size for the patient end opening of the device, as well as upon the cross-sectional area of the entire gas flow path, through which all gas inspired and expired by the patient will pass. As an upper limit it is preferable that the patient end opening not be larger than a hole, 15.8 mm in diameter. 15.8 mm diameter is the internal size of universally used connectors (to masks, etc.) and so the airflow path through any apparatus connected to such a universal connector must ultimately be limited to a maximum of approximately 196 square millimeters (equivalent to cross-section of 15.8 mm diameter hole) at the connection point to such a universal connector. As a lower limit, the patient end opening cannot be so small that it prevents the patient from readily inhaling and exhaling a sufficient amount of gas through it. If the opening becomes too small, the patient is unable to move a sufficient volume of gas through it to support respiration requirements. This principal applies to the most constricted regions of the gas flow path as well; the patient must be able to inhale and exhale a sufficient volume of gas through the device to support respiratory needs and too great a restriction at any point in the gas flow path can prevent these needs from being met. In order to accommodate any size adult patient and the corresponding varying oxygen requirements, applicant suggests that the lower safe limit for the size of the patient end opening is a cross-sectional area of approximately 63 square millimeters (the equivalent cross-sectional of a round hole of 9 mm diameter). Below this size, it becomes questionable whether an adult patient will be able to breathe a sufficient volume of gas though the opening. Similar limitations apply to the entire gas flow path; in a device designed for adult use, no portion of the gas flow path should have a cross-sectional area of less than approximately 63 square millimeters. However, it might be preferable to consider a smaller patient end opening size or a more constricted gas flow path when designing devices specifically for use with infants, small children, etc.

With minimal experimentation, it is clear that for a given flow of injected supplementary respirable gas, a higher static pressure is achieved at the measurement point as the patient end opening decreases in size. Referring to FIG. 13, Table 1, the relationship between static pressure and patient end opening size is illustrated. In attempting to optimize usage of supplementary respirable gas, use of the smallest safe patient end opening size is therefore indicated if maximizing static pressure were the only factor to consider.

However, experimentation in the dynamic mode also revealed, as expected, that the smaller the patient end opening, the greater the fluctuation of pressure at the measurement location throughout the breathing cycle. Referring to FIG. 14, Table 2, the relationship between pressure fluctuation and patient end opening size is illustrated. We can see from table 2, that a large increase in pressure fluctuation occurs as we reduce the size of the patient end opening. The difference in moving from an 11 mm diameter opening to a 10.2 mm diameter opening is an increase of approximately 86% in the fluctuation delta. Therefore, in order to achieve a desirable balance emphasizing both minimizing supplementary respirable gas usage and minimizing pressure fluctuations throughout the breathing cycle, as well as to afford a margin of certainty that enough gas can pass through the opening to support easy adult respiration, applicant has chosen a round opening of 11 mm in diameter as preferable for his examples below, not so small as to deprive the patient of sufficient respirable gas or to dramatically increase pressure fluctuations but small enough to significantly reduce consumption of the available supplementary respirable gas supply.

Experimentation with the architecture around the patient end opening revealed that devices utilizing a frustum-shaped wall surrounding the patient end opening yield more desirable pressure characteristics than devices utilizing the respective tubular conduit leading to the patient end opening. According to one definition, a tube is a long hollow and typically cylindrical object, used for the passage of fluids or as a container. Applicant means to include hollow conduits with non-cylindrical (e.g. square, octagonal, etc.) interiors in the definition of the word "tube." "Tube" is here meant to include any shape conduit with substantially steady internal cross-sectional area and internal shape throughout its length.

A regular pyramid is one whose base is a regular polygon whose center coincides with the foot of the perpendicular dropped from the vertex to the base. A frustum of a regular pyramid is a portion of the regular pyramid included between the base and a section parallel to the base.

A right circular cone is one whose base is a circle whose center coincides with the foot of the perpendicular dropped from the vertex to the base. A frustum of a right circular cone is a portion of the right circular cone included between the base and a section parallel to the base.

Applicant is herein defining "concave frustum-shaped wall" to mean a wall with the shape of the inner surface of a frustum. The outer surface of the frustum wall would be considered to be convex by this definition and is not what is being referenced. The body of applicant's device exhibits a wall that has the shape of the inner concave surface of a frustum. The shape of the exterior surface of this same wall has little bearing on the airflow and pressure characteristics within and through the device.

Figure 4C:
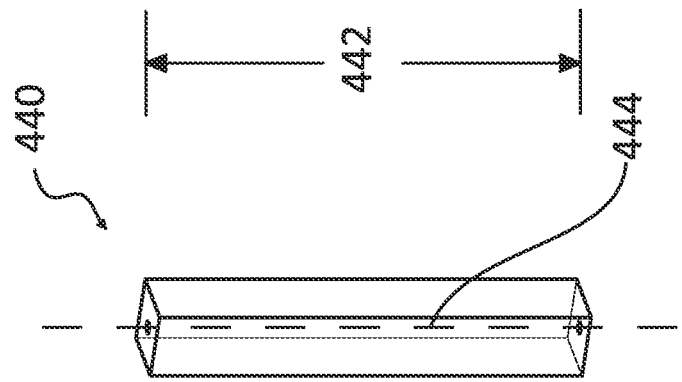
FIGS. 4A, 4B, and 4C compare a regular square pyramid, a regular square pyramidal frustum and a square tube.
Figure 4B:
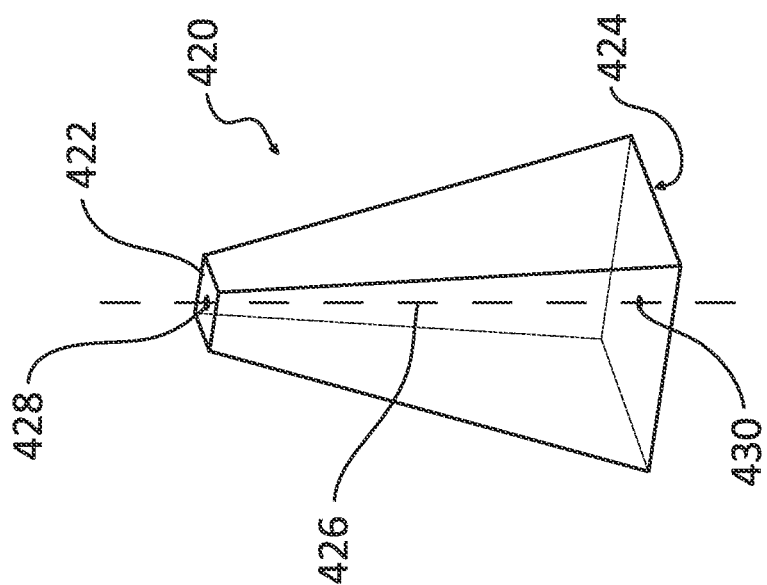
Figure 4A:
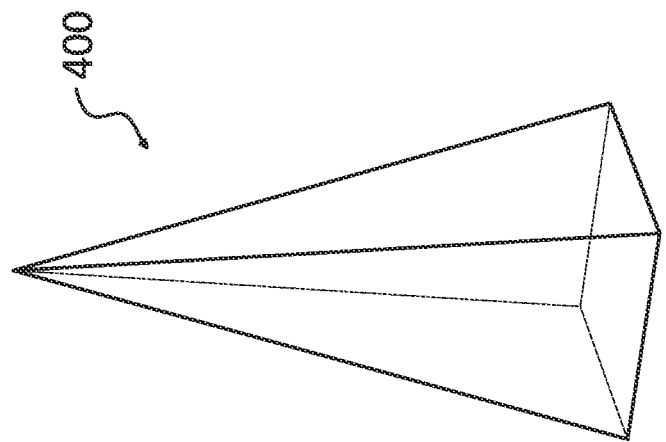

Referring to FIG. 4A, a regular square pyramid 400 is shown. Referring to FIG. 4B, a frustum 420 of the same regular square pyramid is shown. The square pyramidal frustum 420 has narrow end 422, wide end 424 and a central axis 426 passing through the geometric centers 428/430 of the top and bottom square faces 422/424. Referring to FIG. 4C, a square tube is shown. The narrow end 422 of the frustum 420 has the same cross-sectional area as the respective square tube 440 has along its entire length 442.

Figure 5C:
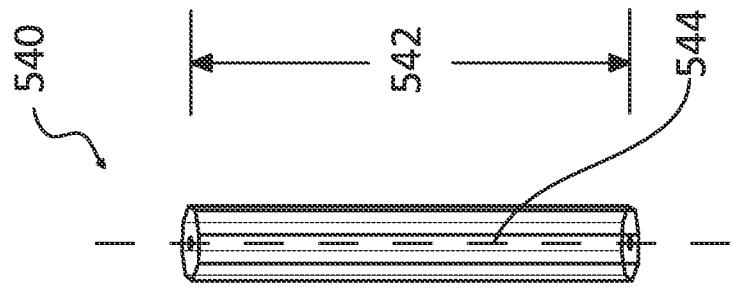
FIGS. 5A, 5B, and 5C compare a regular octagonal pyramid, a regular octagonal pyramidal frustum, and a regular octagonal tube.
Figure 5B:
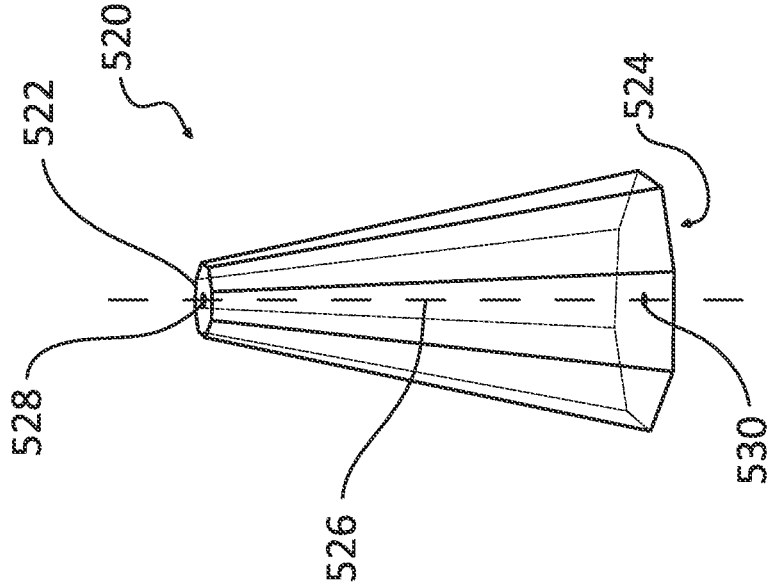
Figure 5A:
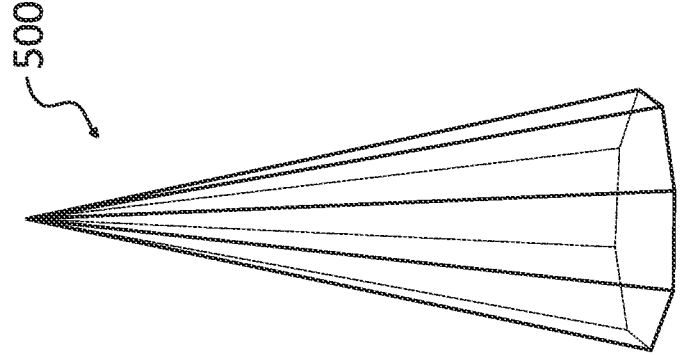

Referring to FIG. 5A, a regular octagonal pyramid 500 is shown. Referring to FIG. 5B, a frustum 520 of the same regular octagonal pyramid is shown. The octagonal pyramidal frustum 520 has a narrow end 522, a wide end 524 and a central axis 526 passing through the geometric centers 528, 530. Referring to FIG. 5C, an octagonal tube 540 is shown. The narrow end 522 of the frustum 520 has the same cross-sectional area as the respective octagonal tube 540 has along its entire length 542.

Referring to FIG. 15, Table 3, examples of results of experiments comparing tubular structures with frustum-shaped walls are tabulated. A device utilizing a conical frustum-shaped wall surrounding the patient end opening yielded more desirable pressure characteristics as compared with the corresponding device utilizing an even-diameter, cylindrical tubular conduit leading to the patient end opening. Similar improvements in desired characteristics were obtained when using a regular square pyramidal frustum-shaped wall as compared to its counterpart square tubular wall with steady cross-sectional area throughout its length. Likewise, improvements in desired characteristics were obtained when utilizing a regular octagonal pyramidal frustum-shaped wall as compared to the respective octagonal tubular wall.

After determining that a frustum-shaped wall yielded improved characteristics as compared with a tubular wall (defining an even cross-sectional area throughout its length), experimentation was then undertaken to determine the optimum angle of the frustum-shaped wall in relation to its central axis in order to yield the most desirable pressure characteristics. Referring to FIG. 6A, a right circular cone 600 is shown. The apex 602 is located directly above the center 604 of the circular base 606 of the right circular cone 600. The central axis 608 is an imaginary line through the apex of the cone straight down through the center 604 of the circular base 606. The central axis forms angle x 612 with the wall of the cone 610. All cones and frusta depicted for mathematical explanatory purposes have been represented in their standard upright position for ease of understanding. In use, the frustum-shaped wall of the device would most likely not be in this orientation.

Referring to FIG. 6B, a frustum 620 of the same right circular cone is shown. The right circular conic frustum 620 has narrow end 622, wide end 624 and a central axis 626 passing through the geometric centers 628/630 of the narrow end 622 and wide end 624. Referring to FIG. 6C, a cylindrical tube 640 is shown. The narrow end 622 of the frustum 620 has the same cross-sectional area as the respective cylindrical tube 640 has along its entire length 642. Again, as with the right circular cone 600, the wall 632 of the frustum 620 makes angle x 634 with the central axis 626.

Utilizing a conical frustum-shaped wall surrounding an 11 mm diameter circular patient end opening and injecting supplementary respirable gas through a 0.65 mm diameter circular jet orifice, located at 47 mm along the central axis from the patient end opening, the pressure characteristics were tested through a range of frustum angles (i.e. the size of frustum angle x, as illustrated in FIG. 6B, was varied and devices comprising the resulting frustum-shaped walls were tested). Referring to FIG. 16, Table 4, the relationship between the angle of the frustum-shaped wall and pressure characteristics is shown. Experimentation with various conical frustum shaped walls revealed that a desirable pressure characteristic (reduction in pressure fluctuation) increased as the frustum-shaped walls were angled up to 4 degrees from the central axis and then desirable characteristics began to diminish during the further increase up to 7 degrees. When the wall was configured at an angle x greater than 7 degrees away from the central axis, the air began to buffet, producing unacceptable pressure characteristics. Within the range of angles greater than 0 and less than 8 degrees from the central axis, it can be seen that the lowest fluctuations from high to low pressure during the breathing cycle were obtained utilizing a frustum-shaped wall angled at 4 degrees from the central axis.

In order to optimize the position of the gas jet 124 and the size of the orifice 110, experimentation was performed utilizing a right circular conic frustum-shaped wall with angle x 634 of 4 degrees and an 11 mm diameter circular patient end. With minimal initial experimentation regarding the placement of the gas jet 124, it became immediately obvious that the highest static pressures per unit of supplementary gas used would be obtained where the gas jet 124 was located approximately along the central, longitudinal axis 122/626 of the interior wall 102/632 that is shaped as a frustrum, relatively near to the wide end 120/624 and directed towards the narrow end 104/622 such that, in use, some portion of the gas flow would be oriented directly towards the narrow end 104/622 without impinging on the interior wall 102. Off-center placement of the gas jet 124 (i.e., not along the central, longitudinal axis 122) yields a functional but less efficient devices. Placing the gas jet 124 a distance away from the narrow end 104/622 is also inefficient and provides little CPAP produced per amount of supplementary gas utilized. And not orienting the gas jet 124 substantially directly towards the narrow end 104/622 also yielded inferior results. This last point in particular distinguishes the present invention from prior art disclosures, such as those by Boussignac referred to above, which teach the requirement of a deflection face as a means to deflect the jet(s) before the supplementary gas flows onward towards the patient end of the device.

Tests were performed using 3 different diameter circular orifice 110 sizes: 0.58 mm, 0.65 mm and 0.79 mm diameter. The gas flow was adjusted to maximum flow rate using a 50 PSI industry standard gas supply for each diameter orifice 110. For the 0.58 mm diameter orifice, the flow rate was 12.0 LPM, for the 0.65 mm diameter orifice, the flow rate was 13.0 LPM, and for the 0.79 mm diameter orifice, the flow rate was 18.0 LPM. Each of the orifice 110 sizes was also tested at various distances from the narrow end 104. And this testing was performed with 4 different size cylindrical-walled prototypes as well as with 3 different size prototypes with frustum-shaped walls. Referring to FIGS. 17, 18 and 19, some of the significant results of this experimentation are tabulated in Tables 5, 6, and 7. Examining Tables 5, 6 and 7, one can see the results of many different parameter shifts upon static pressure and fluctuation. Although there are many possible workable choices revealed by the information expressed in these charts, applicant has selected for his examples below, an 11 mm diameter round patient end opening surrounded by a conical frustum-shaped wall with a wall angle of 4 degrees to the central axis, a gas jet 124 with a 0.65 mm diameter orifice 110, located at 47 mm along the central axis from the patient end opening. As can be seen from table 6, this choice yields a static pressure of 9.5 mm H2O with a fluctuation of only 1.5 mm H2O throughout the breathing cycle while using only 13 LPM of supplementary gas.

The performance of commonly used CPAP devices is disclosed in an article titled Pneumatic Performance of the Boussignac CPAP System in Healthy Humans, by Maria Sehlin, et al. Commonly used devices such as the 10-57003 Mercury Flow-Safe CPAP system or the 5570.13 Boussignac CPAP device require 25 liters per minute of oxygen to generate 8.5 to 10 Cm H2O CPAP pressure. Referring to FIGS. 20 and 21, comparisons between applicant's invention and these 2 other prior art devices are tabulated in tables 8 and 9. Applicant's invention only requires approximately 12.5 liters per minute (50% of previously required flow) to generate the same CPAP pressure. Further, where each of the devices is tested at a flow rate that produces 10 cm H2O static pressure, the pressure fluctuation within either the 10-57003 Mercury Flow-Safe CPAP system or the 5570.13 Boussignac CPAP device is approximately twice that of the present invention.

Based on the above data, applicant has designed an optimized device. Referring to FIG. 1, a cross-section of an embodiment of the breathing assistance device 100 is shown 100. The interior wall 102 that is concave frustum-shaped terminates at the narrow end 104 with an 11 mm diameter. The interior wall 102 that is concave frustum-shaped forms an angle of 4 degrees with the central, longitudinal axis 122. The patient connector 106 connected at the narrow end 104, as shown, is a universal connector with 15.8 mm inner diameter. The patient connector 106 in this example is designed to be engaged indirectly with the breathing tract of a patient via a 15 mm female/22 mm male industry standard patient connection. The patient connector 106 is therefore adapted to be engaged with the external end of an endotracheal tube, a tracheostomy tube, mouthpiece, mask or the like, so that the device may be incorporated into the breathing path of a patient. However, the patient connector 106 is also be adapted to engage with the patient's breathing tract directly if desired. Alternatively, the patient connector is connected directly to other equipment.

The gas jet 124 is preferable located along the central axis of the interior wall 102 and directed along the central, longitudinal axis 122 towards the patient connector 106, with the orifice 110 located at 47 mm from the patient connector 106. The orifice 110 has an inner diameter of 0.65 mm. In use, the gas jet 124 is supplied supplementary respirable gas from a respirable gas source (not shown) via the gas input port 112. The interior wall 102 defines a frustum-shaped interior space 114. This example, breathing assistance device 100 has an interior wall 102 that is concave conical frustum-shaped, approximately 47 mm in length measured along the frustum's central axis and with an interior diameter that varies from approximately 11 mm at the narrow end 104 (i.e., narrow end of frustum) to 17.5 mm at its wide end 120. This interior wall 102/632 makes an angle x of approximately 4 degrees with the central, longitudinal axis 122/626 of the corresponding frustum 620.

In this example, an endcap structure 118 provides housing and support for the gas jet 124 and the gas input port 112. The interior space 114 is in fluid communication with the atmosphere via atmospheric openings 116 through the endcap structure. Referring to FIG. 2, the location of the atmospheric openings 116 is illustrated. Applicant defines "fluid communication" as to include movement through a valve, a filter, or the like, or any other arrangement which allows substantially unimpeded exchange of gas between the interior of the device and the atmosphere.

In some embodiments, the gas jet 124 also exhibits a concave frustum-shaped wall in its interior, that varies from 3 mm diameter at the point of connection to the gas input port 112 to 0.65 mm diameter at the orifice 110. The gas jet 124 is, in some embodiments, 19.8 mm long measured axially. In such, the internal frustum-shaped wall of the gas jet 124 makes an angle of 3.4 degrees with the central, longitudinal axis 122 of the gas jet 124.

The above detailed measurements describe a non-limiting example and the device may of course be of any suitable size, shape and configuration within the spirit of the invention.

In use, supplementary respirable gas is directed through the gas jet 124 out the orifice 110 through the interior space 114 towards the narrow end 104. The gas jet 124 creates an increased pressure, particularly near the narrow end 104 and through the patient connector 106 and into the patient's airway. Upon inhalation, the patient breathes in supplementary respirable gas that enters the interior space 114 through the orifice 110 as well as atmospheric air that is drawn into the interior space 114 though the atmospheric openings 116. Upon exhalation, the expired air exits from the patient through the patient connector 106, through the narrow end 104, through the interior space 114, and finally exiting the breathing assistance device 100 through the atmosphere openings 116.

The gas input port 112 of this embodiment is designed to be engaged via a standard connecting tube (not shown) with a source of supplementary respirable gas (not shown). The pressure delivered to the patient at any given moment will be dependent upon the pressure of the respirable gas entering the interior space 114 via the gas jet 124 as well as upon the transient flows of gas due to the patient's inhalation and exhalation through the interior space 114 during respiration. With an appropriate pressure from the supplementary respirable gas source, CPAP (continuous positive airway pressure) is produced for the patient. At lower pressures from the supplementary respirable gas source, a more passive supplementation of respirable gas may be provided to the patient. The flow of supplementary respirable gas through the gas jet 124, and the resulting pressure within the device, may be controlled externally with a flow meter, a pressure regulator, or the like.

Figure 9:
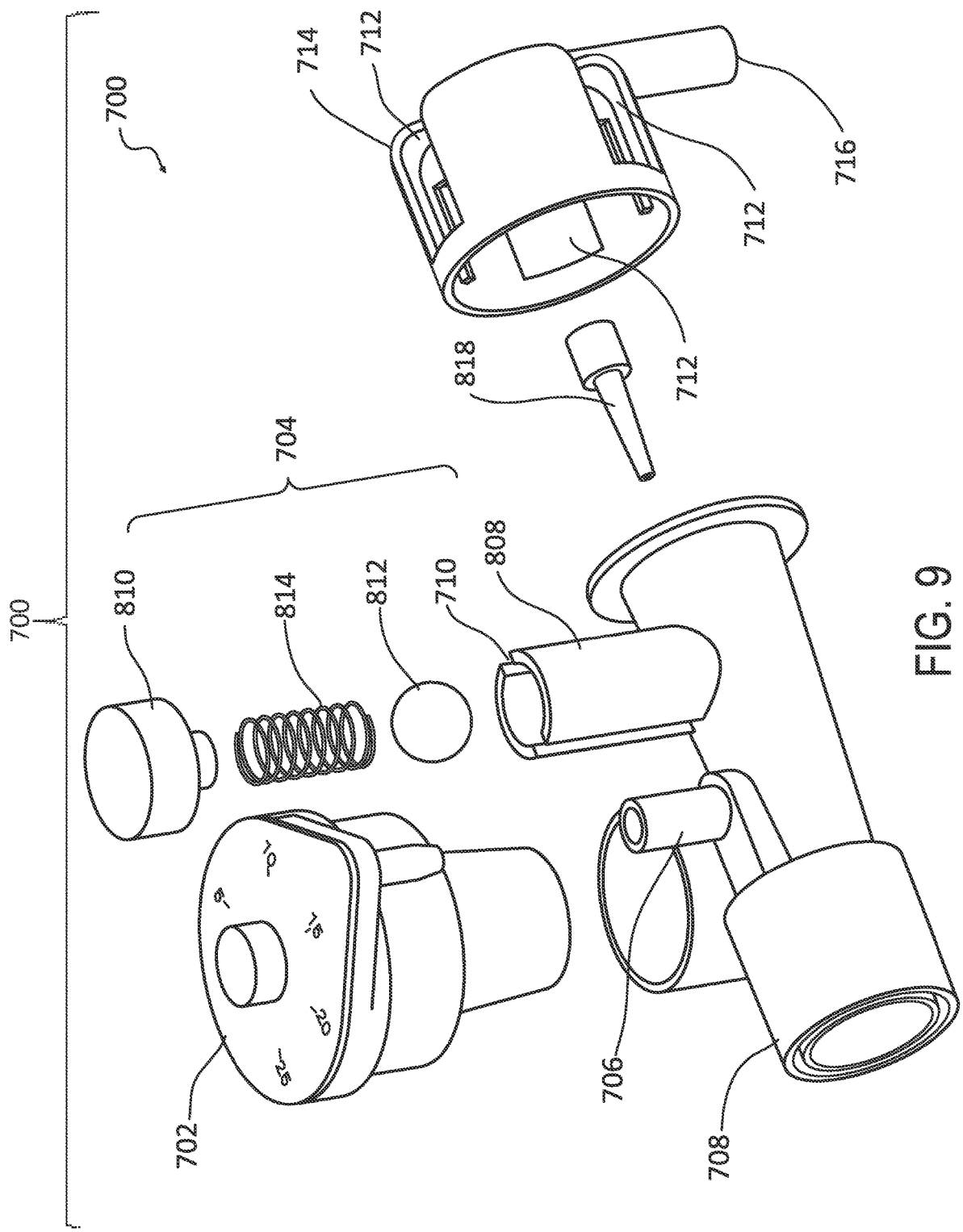
FIG. 9 shows an isometric exploded view of an example of a breathing assistance device with manometer and pressure relief valve according to the present invention.

Referring to FIGS. 7, 8 and 9, a second example of the present invention 700 has essentially the same structure as the example above, further including a manometer 702 and a pressure relief valve 704. The modified walls 806 include a manometer port 802 for attaching a manometer 702, disposable or otherwise, to measure the pressure just beyond the patient end opening 820 within the industry standard patient connector 708 via the pressure measurement channel 802. The sensing port of the manometer 702 is press fit, glued or otherwise firmly seated to the manometer port 706. The manometer 702 gives a continuous immediate display of the pressure inside the industry standard patient connector 708 near the patient end of the device 700. The currently described and illustrated configuration provides a readily discernible display. Such a prominent and easily perceived indication of internal pressure provides both convenience for one monitoring and/or applying the device, as well as added safety for the patient.

This example 700 of the invention further comprises a ball and spring pressure relief valve 704. A pressure relief through hole 804 made through the concave frustum-shaped wall 806 of the device 700. A pressure relief valve housing 808 with endcap 810 encases the ball 812 and spring 814 mechanism and is attached to the outer surface of the frustum-shaped wall 806 covering the through hole 804 such that the spring 814 presses the ball 812 into the through hole 804 through the frustum-shaped wall 806, blocking gas from escaping through the through hole 804. The spring 814 is calibrated such that it holds the ball 812 in position blocking the through hole 804 until a threshold pressure is reached within the interior space 816. When the pressure within the interior space 816 rises to or above the threshold pressure, the spring 814 is compressed as the ball 812 is pushed away from the through hole 804 by the pressurized gas within the interior space 816, allowing gas to escape the interior space 816 and out through the 2 pressure release vents 710 in the side of the pressure relief valve housing 808, thereby decreasing the excess pressure within the interior space 816. When the ball 812 is in place, the ball 812 closes the interior space 114 of the interior wall 102, maintaining a continuous interior wall 102 per some embodiments.

An example of an appropriate threshold pressure for CPAP application of a device constructed according to this example would be 25+/−5 cm H2O, but an appropriate range might be anywhere from 15 to 45 cm H2O depending upon preference and application. Thus, a safety pressure relief is provided in the case of overpressure within the interior space 816 e.g., because the atmospheric openings 712 are blocked by an obstruction, etc. This pressure relief valve 704 affords an added measure of safety for the patient. However, the atmospheric openings 712 are positioned around the sides and proximal surface of the end cap 714 such that the likelihood of an object inadvertently obstructing the fluid communication path between the interior space 816 and the atmosphere is decreased.

The "ball and spring" mechanism of the pressure relief valve 704 as described above is a non-limiting example of a pressure relief mechanism. Other types of safety pressure relief mechanisms known in the art may be used, such as for example, a safety sleeve as described in U.S. Pat. No. 5,036,847. Even an open hole might be utilized to afford additional protection from overpressure to the patient. There are, of course, numerous other possibilities that could be employed within the scope of the invention. And any such pressure relief mechanism could likewise be placed in alternative locations within the device 700 to provide an additional safety pressure relief in the event of overpressure within the interior space 816 of the device.

The input port 716 of this embodiment is designed to be engaged via a standard connecting tube (not shown) with a source of supplementary respirable gas (not shown). The pressure delivered to the patient at any given moment will be dependent upon the pressure of the respirable gas entering the interior space 816 via the jet 818 as well as upon the transient flows of gas due to the patient's inhalation and exhalation through the interior space 816 during respiration. With an appropriate pressure from the supplementary respirable gas source, CPAP (continuous positive airway pressure) is produced for the patient. At lower pressures from the supplementary respirable gas source, a more passive supplementation of respirable gas may be provided to the patient.

The dimensions of the breathing assistance device with manometer and with pop-off safety relief valve 700 are similar to those of the first example. The manometer 702 and pressure relief valve 704 can be included with minimal incursion into the interior space 816 and minimal distortion of the frustum-shaped wall 806. A 7 mm diameter through hole 804, which is completely blocked by a portion of the ball 812, is all that is required for the pressure relief valve 704 while a pressure measurement channel 802 that opens into the interior space of the industry standard patient connector 708 is all that is required internally in order to allow successful pressure measurement via the manometer 702. Otherwise only external additions that do not encroach into the interior space 816, such as the manometer 702, the manometer port 706, the pressure relief valve housing 808, the spring 814, and the endcap 810 are required.

The examples given above are meant to be non-limiting examples of ways to practice the current invention. Many varied embodiments may be conceived which fall within the scope and spirit of the present invention.

Variations

One definition of a frustum is "a truncated cone or pyramid in which the plane cutting off the apex is parallel to the base." Another definition is "the portion of a solid (normally a cone or pyramid) that lies between two parallel planes cutting it. The prototypes and examples discussed above comprise concave substantially frustum-shaped walls where the relevant frustum would satisfy either of the above definitions.

In constructing prototypes for these experiments only frustums of regular pyramids and right regular cones have been utilized by applicant. A regular pyramid is one whose base is a regular polygon whose center coincides with the foot of the perpendicular dropped from the vertex to the base. Applicant defines this perpendicular, dropped from the vertex to the base, as being the central axis of the frustums of right regular pyramids discussed herein. A right circular cone is a circular cone whose axis is perpendicular to its base. Applicant defines this axis as being the central axis for the frustums of right regular cones discussed herein.

Most generally, a frustum is "the portion of a solid (normally a cone or pyramid) that lies between two parallel planes cutting it." Another more limited definition of a frustum is "a truncated cone or pyramid in which the plane cutting off the apex is parallel to the base." Applicant defines the frustum of a regular pyramid as "the portion of a right regular pyramid included between the base and a section parallel to the base." Applicant defines the frustum of a right circular cone as "that portion of the right circular cone included between the base and a section parallel to the base."

We can readily interpolate from the results tabulated in FIG. 15 Table 3 that we could obtain desirable improvement in pressure characteristics with any regular polygonal wall, where n is greater than or equal to 4, by moving from a steady cross-sectional area type ("tubular") device to a device with a frustum-shaped wall of the corresponding type. If it works for a square, an octagon and a circle, as our experiments show, we can be quite certain it will work for any regular n-sided polygonal type wall where n is between 4 and infinity (the circle). We can also extrapolate that we will obtain similar improvement with a regular triangular pyramidal frustum-shaped wall as compared with the respective triangular tube.

Figure 10:
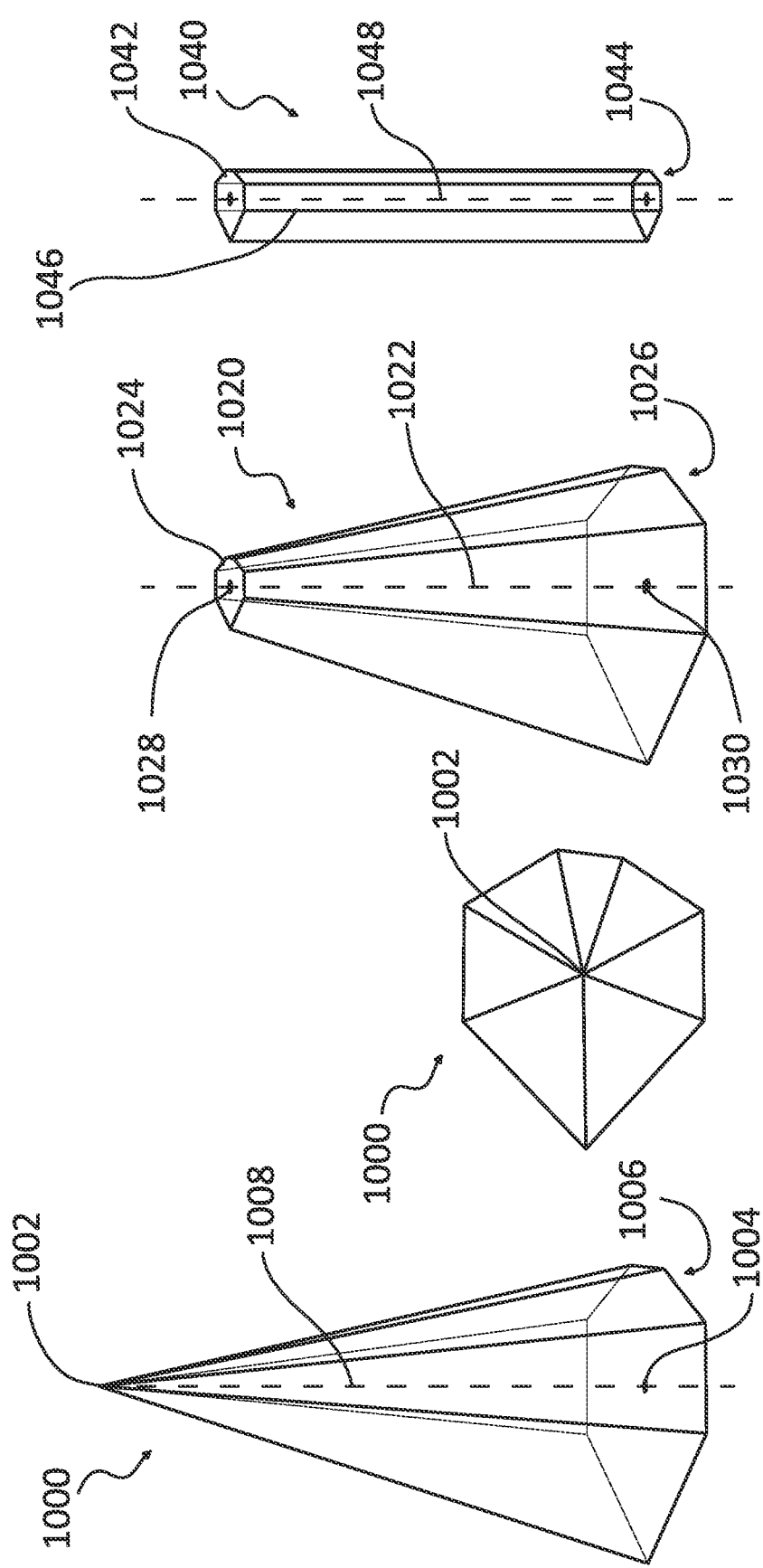
FIGS. 10A, 10B, 10C, and 10D compare an irregular heptagonal pyramid, an irregular heptagonal pyramidal frustum, and an irregular heptagonal tube.

And we can further assume that we would also obtain similar improvement by "angling out" the wall of many, if not all, steady cross-sectional area enclosing walls we might choose to surround the patient connector 106. Referring to FIGS. 10A and 10B, a side view and a top view of an irregular pyramid 1000 are shown respectively. In this case, the vertex 1002 is located directly above the centroid 1004 of the base 1006 and the central axis 1008 is shown. In discussing right circular cones and regular pyramids, the geometric center of the base is easily located. Locating the centroid of an irregular polygon may be a bit more complicated.

Referring to FIG. 10C, a frustum 1020 of the irregular pyramid with central axis 1022 is shown. The top face 1024 of the frustum is an irregular heptagon as is the base 1026. The centroid 1028 of the top face 1024 as well as the centroid 1030 of the base 1026 are indicated. The central axis 1022 passes through these two points 1028, 1030.

Referring to FIG. 10D, an irregular "tubular" structure is shown. The top face 1042 and bottom face 1044 both have the exact same shape and dimensions as the top face 1024 of the irregular pyramidal frustum 1020. Any horizontal cross-section of the "tube" has the exact same shape and dimensions as the top face 1024 of the irregular pyramidal frustum 1020. Therefore, the irregular tube 1040 defines a steady cross-sectional area throughout its length. If one were to construct 2 prototype breathing assistance devices; one having a concave frustum-shaped wall as in FIG. 10C 1020 with a patient end opening being the top face 1024, and the second prototype using the irregular tube-like structure 1040 represented in FIG. 10D; based on the data from applicant's experimentation as described above, we would expect better performance from a breathing assistance device which utilizes the frustum-shaped wall as in FIG. 10C, particularly if some side faces make an angle with the central axis 1022 of approximately 4 degrees.

And likewise we would anticipate achieving some measure of improvement by angling out some portion less than the entire enclosing wall. In other words, if we began with a tubular structure such as is represented in FIG. 10D 1040, and angled some but not all of the side faces 1046 away from what would be the patient end opening 1042 at an angle greater than 0 degrees and less than 8 degrees from the central axis 1048, some measure of improvement over the straight tubular structure 1040 would still be expected in this application. An infinite number of irregular pyramidal or deformed conic structures of this type could be readily conceived and we would anticipate improvement where we move from a tubular-type structure (at 0 degrees with respect to the central axis and defining a steady cross-sectional area along its length) to a structure with some portion of the wall surrounding the patient end opening angled away from the opening at greater than 0 degrees and less than 8 degrees. In other words applicant asserts that if there is a cross-section through the wall surrounding the patient end opening and which includes the central axis, where the wall surrounding the patient end opening makes an angle of more than 0 and less than 8 degrees with the central axis, then improvement in desired pressure characteristics would be expected over the comparable "tubular" structure.

Further, the concave frustum-shaped wall 102, 806 need not be completely symmetrical, smooth or regular. The substantially frustum-shaped wall may include reservoir areas, bends, curves, texturing, etc. as desired, while still remaining within the scope of the present invention. And thus the present inventive concept of obtaining improved CPAP pressure characteristics by utilizing angled walls surrounding the patient end opening, as opposed to utilizing a wall that defines interior space with a steady cross-sectional area, can be applied in many varied ways to an infinite number of differently shaped bodies in order to accomplish application of the present invention.

The examples above utilize a fully rotationally symmetric in which the interior wall 102 forms a conic frustum-shaped, 806 with the narrow end 104/820 leading directly into a patient connector 106/708 that is slightly tapered, substantially straight creating a very efficient streamlined structure which results in highly efficient performance. However, the invention can clearly be practiced in many and varied ways, most obviously with any regular polygonal pyramidal frustum-shaped wall, as well as with irregular concave frustum-shaped walls.

Although the above examples illustrate the connector 106/708 being an Industry Standard Patient Connection designed to be engaged with a standard connector (for attachment to a mask, an endotracheal tube, etc.), the connector 106/708 may alternatively be molded to any desired shape and size for the purpose of engaging with the breathing tract of the patient. For example, the connector 106/708 may be molded into a mask, a mouthpiece, an endotracheal tube, etc. The connector 106/708 may be straight, curved, narrow, wide, etc., and have whatever type of internal and external architecture that is preferred. Or one might choose to make the narrow end 104/820 of the interior wall 102 be frustum-shaped and somewhat wider and then narrow the gas-flow path to a smaller cross-section at the narrow end 104/708. A configuration such as this might take on many forms and still remain within the scope of the present invention.

Figure 11:
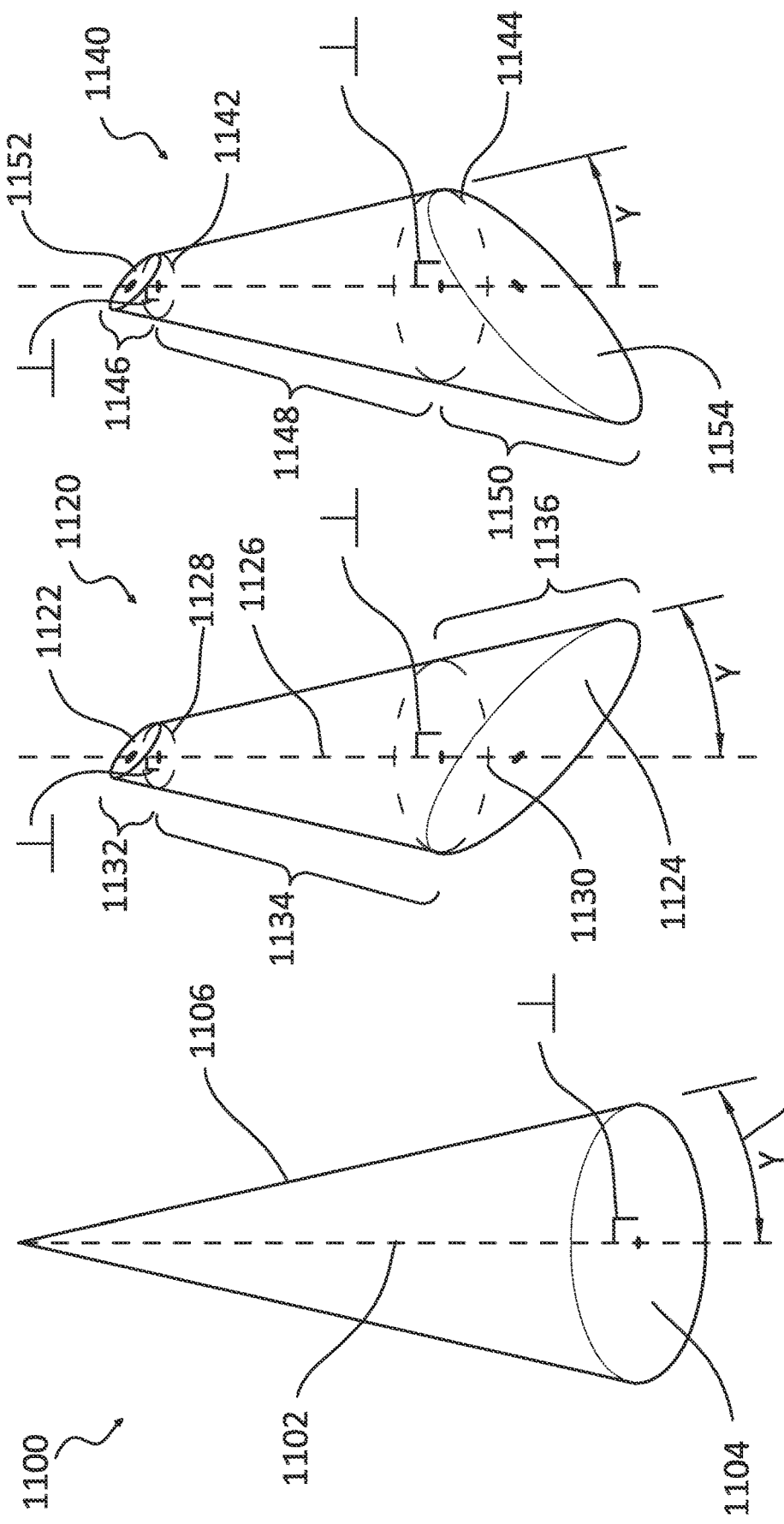
FIGS. 11A, 11B, and 11C compare a right circular cone, conic frustums and conic portions.

Referring to FIG. 11A, a right circular cone with central axis 1102 is shown 1100. The cone has a base 1104 and sidewall 1106. The sidewall 1106 makes angle y 1108 with the central axis 1102. Referring to FIG. 11B, a frustum of the same cone 1100, according to a more general definition of frustum, is shown. The frustum has an elliptical top face 1122 and a parallel elliptical bottom face 1124, each making congruent angles with the central axis 1126 of the corresponding cone 1100. Cutting cross-sections 1128,1130 through the frustum 1120 perpendicular to the axis 1126 of the corresponding right circular cone divides the structure into 3 portions, a top segment 1132, a middle portion 1134 and a bottom portion 1136. The middle portion 1134 resulting from this division is a frustum of a right circular cone with the same central axis 1126 as the corresponding cone 1100.

One might desire to use a wall with a shape 1120 such as that shown in FIG. 11B to practice the present invention. However, the geometry reveals that this shape 1120 reduces to a middle frustum-shaped portion 1134 and top and bottom portions 1132, 1136. In such a case, the top smaller circular face 1128 of the frustum-shaped middle portion 1134 could be considered to be the concave frustum-shaped wall with central axis 1126, while the top portion 1132 could be considered to be part of the connector 106, 708. The lower portion 1136 might have little to do with the pressure characteristics of the device especially if it is located further away from the patient end connector 106/708 than the jet orifice 110/822.

Referring to FIG. 11C, a portion of a right circular cone 1140 is shown. Unlike FIG. 11B, this right circular cone 1140 is not a frustum even according to the most general definition. However, as in the previous example, this right circular cone 1140 may be divided with cross-sections 1142/1144 parallel to the base 1104 of the corresponding right circular cone 1100 to yield a middle frustum-shaped portion 1148 and top and bottom portions 1146/1150. As in the above example, if desired to use a shape such as that represented here (right circular cone 1140 to construct a breathing assistance device according to the present invention, the middle portion 1148 could be viewed as the frustum-shaped wall with patient end opening 1142 while the top portion 1146 could be viewed as part of the connector 106/708. Again, the lower portion 1150 might have little to do with the pressure characteristics of the device especially if it is located further away from the narrow end 104/820 than the jet orifice 124/822.

The same mathematical logic can be applied similarly to reduce irregular pyramidal type shapes.

Figure 12:
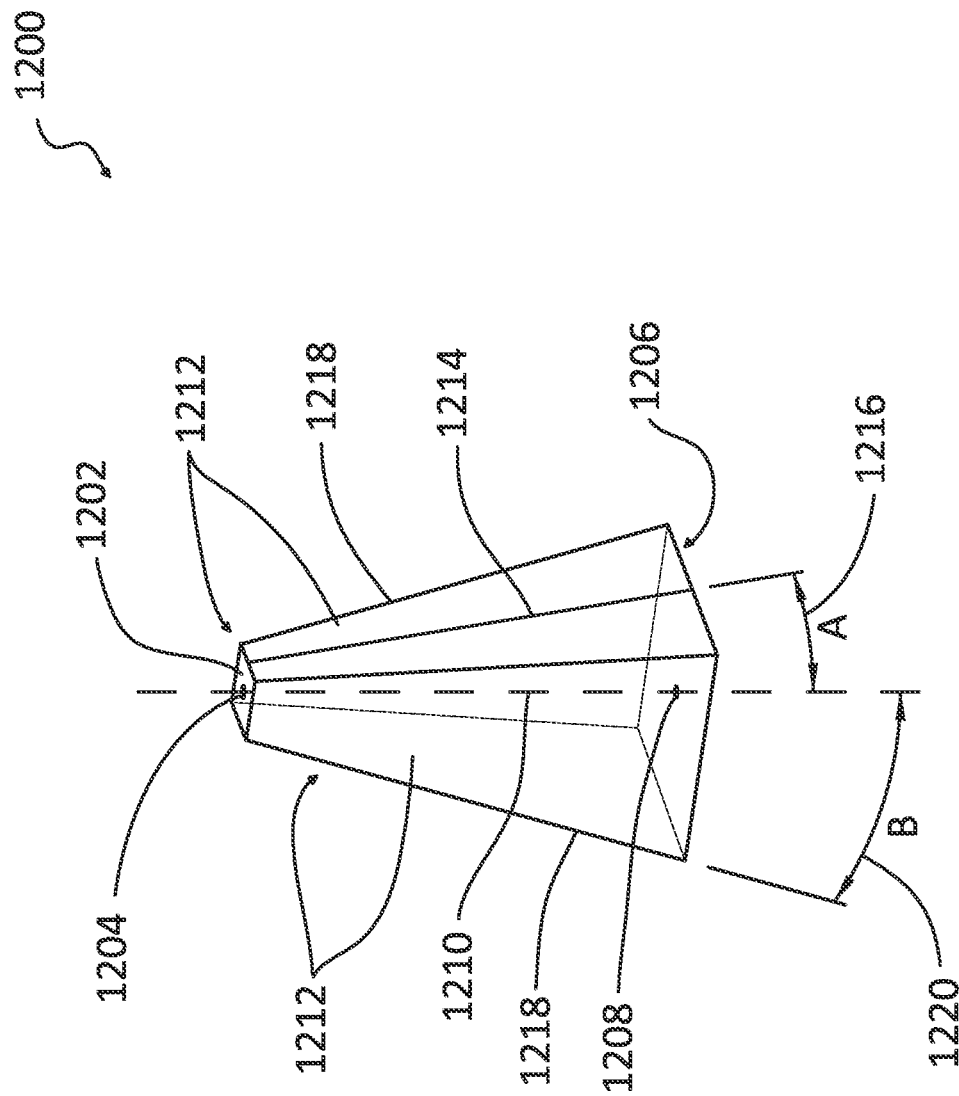
FIG. 12—Illustrates the variation of the angle between the central axis and various locations on a side face of a pyramidal frustum.

FIG. 12 illustrates the variation of the angle between the central axis and various locations on a side face of a pyramidal frustum. Referring to FIG. 12, a frustum 1200 of a regular square pyramid is shown. The frustum 1200 has a square top face 1202 with center 1204 marked and a square bottom face 1206 with center 1208 marked. The central axis 1210 runs through the center 1204 of the top face 1202 and the center 1208 of the bottom face 1206. The frustum has 4 side faces 1212. A line 1214 drawn down the center of a side face 1212 makes angle A 1216 with the central axis 1210. The frustum also has 4 edges 1218 where the side faces 1212 meet each other. A side edge 1218 of a side face 1212 of the frustum 1200 forms angle B 1220 with the central axis 1210. We can see that angle B 1220 and angle A 1216 are not equivalent and that angle B 1220 is greater than angle A 1216. For example, where angle A 1216 is 4 degrees, angle B 1220 is 5.65 degrees.

This illustrates that when dealing with non-conic frustums (e.g., shapes 420/520/1020/1200) the angle made between the frustum wall and the central axis will vary depending upon where on the wall the measurement is made. The frustum of the right circular cone 620 is the special case where the wall 632 of the frustum makes a constant angle with the central axis 626 no matter where around the perimeter (circumference) of the wall one measures.

In the above examples, the primary component pieces are from molded polycarbonate plastic. However, plastic formed in this manner is a non-limiting example of a suitable material and the device may be fashioned from any suitable materials, for example styrene, acetal, polypropylene, PVC, etc. Likewise, the pressure relief spring 814 is made from stainless steel but could be fashioned from any flexible metal, plastic or rubber.

In the above examples, the gas input port 112/716 is an integrally molded feature of the end cap 118/714. The manometer port 706 is an integrally molded feature of the main body of the device 700. But alternatively, each could be separate pieces attached by adhesive, mechanical fastening, ultrasonic welding, etc.

In the above examples, the inlet of the manometer pressure measurement channel 802 is located just beyond the patient end opening 820 within the connector 708 and the manometer port 706 is located approximately one third of the way along the length of the frustum-shaped wall 806 from the patient end opening 820. This is a non-limiting example of the placement of the manometer channel 802 and manometer port 706. A manometer 702 and a pressure tap 802 could be placed in any suitable desired location in fluid communication with the industry standard patient connector 708. And likewise, the manometer 702 may be of the design described in U.S. Pat. No. 5,557,049, by Ratner, or of any other suitable manometer design.

In the above examples, atmospheric openings 116/712 of the device are left open to the atmosphere. However, the atmospheric openings 116/712 need not be left wide open in order for the interior space to be in fluid communication with the atmosphere. For example, a filter could be placed within, over, or within an extension of the end cap 118/714 while still retaining the desired characteristic of fluid communication of the interior space 114/816 with the atmosphere, allowing for exhalation out through the atmospheric openings 116/712, release of excess pressure, as well as influx of fresh atmospheric air into the device. Likewise, other devices that allow fluid communication of the interior space 114/816 with the atmosphere through the atmospheric openings 116/712 could be placed within, over, or as extensions of the atmospheric openings 116/712 while still allowing the desired function.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A breathing assistance device comprising:
a body having an interior wall defining an interior space;
the interior wall having a narrow end and a wide end and having a cross-sectional area that is continuously smaller from the wide end to the narrow end;
a patient connector interfaced to the narrow end, the patient connector adapted to be engaged directly with a patient's breathing tract or adapted to be engaged indirectly with the patient's breathing tract;
a gas jet having a jet orifice located at the wide end of the interior wall and aimed into the interior space, the gas jet adapted to be supplied with a gas from a source of the gas under pressure, the gas jet directing the gas through said interior space substantially along a central, lengthwise axis of the interior space towards the patient connector; and
an annular wall, wherein the annular wall surrounds the gas jet, and the annular wall comprises a plurality of openings placed along the annular wall, wherein each of the plurality of openings extends through an interior surface and an exterior annular surface of the annular wall to allow fluid to communicate between the interior space and an atmosphere outside of the breathing assistance device, wherein a first opening of the plurality of openings is being positioned above the gas jet and a second opening of the plurality of openings is being positioned below the gas jet, and wherein the annular wall interfaced to and extending distally from the wide end of the interior wall.

2. The breathing assistance device according to claim 1, where the cross-sectional area has a square cross-sectional shape or a hexagonal cross-sectional shape.

3. The breathing assistance device according to claim 1, where the interior wall diverges at an angle greater than 0 degrees and less than 8 degrees from the central, lengthwise axis.

4. The breathing assistance device according to claim 1, where the interior wall diverges at an angle greater than 3 degrees and less than 4 degrees from the central, lengthwise axis.

5. The breathing assistance device according to claim 1, where the interior wall diverges at an angle of 4 degrees from the central, lengthwise axis.

6. The breathing assistance device according to claim 1, where the narrow end has the cross-sectional area between 63 and 185 square millimeters.

7. The breathing assistance device according to claim 1, where the narrow end has the cross-sectional area of 95 square millimeters.

8. The breathing assistance device according to claim 1, where the jet orifice is a distance of from between 25 and 70 millimeters from the patient connector.

9. The breathing assistance device according to claim 1, where the jet orifice is a distance of 47 millimeters from the patient connector.

10. The breathing assistance device according to claim 1, where the jet orifice has a diameter of between 0.5 and 1.0 millimeters.

11. The breathing assistance device according to claim 1, where the jet orifice has a diameter of 0.65 millimeters.

12. The breathing assistance device according to claim 1, where the patient connector is a respiratory connector.

13. The breathing assistance device according to claim 1, further comprising a manometer in fluid communication with an edge of the patient connector.

14. The breathing assistance device according to claim 13, further comprising a pressure relief valve in fluid communication with the interior space by way of a pressure relief through hole such that, when the pressure relief valve is closed, the pressure relief through hole is occluded.

15. A method of increasing airflow of a gas from a breathing assistance device according to claim 1, with a given gas volume input, the method comprising: expelling the gas from the gas jet into the interior space at the wide end of the interior space and aimed toward the narrow end of the interior space; and providing a flow of the gas from the narrow end of the body to a patient through the direct or indirect patient interfaces.

16. The method of claim 15, wherein an area within the interior walls of the body forms a frustum.

17. The breathing assistance device according to claim 1, further comprising a manometer, the manometer fluidly coupled with the patient connector at an edge of the patient connector.

18. A breathing assistance device comprising:
- a body having an interior wall defining an interior space, the interior wall having a wide end and a narrow end and a cross-sectional area that continuously narrows from the wide end to the narrow end;
- a patient connector interfaced to the narrow end of the interior wall;
- the interior wall having a central, longitudinal axis passing from a center of the narrow end and a center of the wide end;
- where the interior wall forms a linear angle with the central, longitudinal axis of greater than 0 degrees and less than 8 degrees;
- a gas jet adapted to be supplied with a gas from a pressurized gas source, the gas jet located at the wide end and directing the gas into the interior space at the wide end and aimed towards the narrow end; an annular wall, wherein the annular wall surrounds the gas jet, and the annular wall comprises a plurality of openings placed along the annular wall, wherein each of the plurality of openings extends through an interior surface and an exterior annular surface of the annular wall to allow fluid to communicate between the interior space and an atmosphere outside of the breathing assistance device, and wherein a first opening of the plurality of openings is being positioned above the gas jet and a second opening of the plurality of openings is being positioned below the gas jet, and wherein the annular wall interfaced to and extending distally from the wide end of the interior wall.

* * * * *